US009730854B2

(12) United States Patent
Ren

(10) Patent No.: US 9,730,854 B2
(45) Date of Patent: Aug. 15, 2017

(54) SYSTEM FOR DYNAMICALLY ADJUSTING TREATMENT ANGLE UNDER TENSION TO ACCOMMODATE VARIATIONS IN SPINAL MORPHOLOGY

(71) Applicant: Beijing Ryzur Axiom Medical Investment Co., Ltd., Beijing (CN)

(72) Inventor: Song Ren, Shun Yi District (CN)

(73) Assignee: Beijing Ryzur Axiom Medical Investment Co., Ltd., Beijing (CN)

( * ) Notice: Subject to any disclaimer, the term of this patent is extended or adjusted under 35 U.S.C. 154(b) by 580 days.

(21) Appl. No.: 14/364,476

(22) PCT Filed: Dec. 13, 2012

(86) PCT No.: PCT/CN2012/086566
§ 371 (c)(1),
(2) Date: Jun. 11, 2014

(87) PCT Pub. No.: WO2013/087001
PCT Pub. Date: Jun. 20, 2013

(65) Prior Publication Data
US 2014/0364910 A1    Dec. 11, 2014

(30) Foreign Application Priority Data
Dec. 13, 2011  (CN) .......................... 2011 1 0415599

(51) Int. Cl.
*A61H 1/00*    (2006.01)
*A61F 5/04*    (2006.01)
(Continued)

(52) U.S. Cl.
CPC ............. *A61H 1/008* (2013.01); *A61F 5/042* (2013.01); *A61H 1/0222* (2013.01); *A61H 7/002* (2013.01);
(Continued)

(58) Field of Classification Search
CPC .............. A61F 5/00; A61F 5/04–5/042; A61F 2005/0153; A61H 1/008; A61H 1/02;
(Continued)

(56) References Cited

U.S. PATENT DOCUMENTS

| 6,152,950 A | 11/2000 | Shealy et al. | |
|---|---|---|---|
| 7,462,189 B2 * | 12/2008 | Smith | A61F 5/04 601/24 |
| 2006/0287627 A1 | 12/2006 | Johnson | |

FOREIGN PATENT DOCUMENTS

| CN | 201684129 | 12/2010 |
|---|---|---|
| CN | 201755264 | 3/2011 |

(Continued)

OTHER PUBLICATIONS

"International Application No. PCT/CN2012/086566, International Search Report mailed Mar. 21, 2013", (Mar. 21, 2013), 5 pgs.
(Continued)

*Primary Examiner* — Rachel Young
(74) *Attorney, Agent, or Firm* — Schwegman Lundberg & Woessner, P.A.

(57) ABSTRACT

A system for dynamically adjusting treatment angle under tension to accommodate variations in spinal morphology during spinal decompression therapy is provided. It provides a tensioning device including a patient-positioning means, a tension-producing actuator, a positioning device, a patient interface device, a control system and a display. The control system with feedback on the resultant tension vector applied to patient spine operationally configured to allow for adjustment of either tension producing actuator position, patient position, or both while applying tension to the patient spine during non-therapeutic tension levels. The control system automatically adjusts tension producing actuator work levels such that the resultant tension vector magnitude remains ideally constant during adjustment of resultant tension vec-
(Continued)

tor angle, reducing the risk of eliciting paraspinal muscle contraction due to changes in resultant tension vector magnitude.

17 Claims, 9 Drawing Sheets

(51) Int. Cl.
    *A61H 1/02*     (2006.01)
    *A61H 7/00*     (2006.01)
    *A61F 5/042*     (2006.01)

(52) U.S. Cl.
    CPC ............... *A61H 2001/0233* (2013.01); *A61H 2201/0103* (2013.01); *A61H 2201/0142* (2013.01); *A61H 2201/1215* (2013.01); *A61H 2201/1246* (2013.01); *A61H 2201/163* (2013.01); *A61H 2201/1621* (2013.01); *A61H 2201/1626* (2013.01); *A61H 2201/1652* (2013.01); *A61H 2201/1671* (2013.01); *A61H 2201/5023* (2013.01); *A61H 2201/5038* (2013.01); *A61H 2201/5043* (2013.01); *A61H 2201/5048* (2013.01); *A61H 2201/5061* (2013.01); *A61H 2201/5064* (2013.01); *A61H 2201/5071* (2013.01); *A61H 2203/0437* (2013.01); *A61H 2230/625* (2013.01)

(58) Field of Classification Search
    CPC   A61H 1/0218–1/0222; A61H 1/0292–1/0296; A61H 2001/0207; A61H 2001/0233; A61H 2201/0103; A61H 2201/0142; A61H 2201/1619–2201/163; A61H 2203/0456; A61H 2205/081
    See application file for complete search history.

(56) References Cited

FOREIGN PATENT DOCUMENTS

| | | |
|---|---|---|
| CN | 102188302 | 9/2011 |
| JP | 2007313243 | 12/2007 |
| WO | WO-2007/040775 | 4/2007 |
| WO | WO-2013/087001 A1 | 6/2013 |

OTHER PUBLICATIONS

"International Application No. PCT/CN2012/086566, Intrnational Preliminary Report on Patentability dated Jun. 17, 2014", 5 pgs.
"International Applicaiton No. PCT/CN2012/086566, Written Opinion mailed Mar. 21, 2013", 4 pgs.

* cited by examiner

SYSTEM FOR DYNAMICALLY ADJUSTING TREATMENT ANGLE UNDER TENSION TO ACCOMMODATE VARIATIONS IN SPINAL MORPHOLOGY

PRIORITY CLAIM TO RELATED APPLICATIONS

This application is a U.S. National Stage application filed under 35 U.S.C. §371 from International Application Ser. No. PCT/CN2012/086566, which was filed Dec. 13, 2012, and published as WO 2013/087001 on Jun. 20, 2013, and which claims priority to Chinese Application No. 201110415599.1, filed Dec. 13, 2011, which applications and publication are incorporated by reference as if reproduced herein and made a part hereof in their entirety, and the benefit of priority of each of which is claimed herein.

RELATED APPLICATIONS

The present invention relates to a system that applies tension to a patient's spine to treat the spine related diseases. More specifically, the present invention relates to a positioning correction system that applies tension to a patient's spinal lesion area through a range of angles, and that can adjust the angle dynamically under tension without changing the intended tension, for the purpose of fine tuning treatment angle for each patient.

BACKGROUND OF THE INVENTION

Therapists utilize spinal decompression therapy non-operative in vitro to treat various spinal ailments including herniated discs, degenerative disc disease, sciatica, posterior facet syndrome, and post surgical pain. Decompression therapy is a derivative of traditional traction-based therapy, whereby the spine is pulled by an outside force (such as by a therapist manually or by an automated process). The spine is typically held in a continuous state of tension during traditional traction-based therapy. Decompression therapy differs from traditional traction therapy in that tension is applied to the spine at a specific angle. Also, during decompression therapy, various tensile forces are applied or cycled throughout the treatment period such that paraspinal muscles are relaxed and fatigued, allowing for interdiscal separation. These functions provide for a smooth transition between different levels of tension. In either traditional traction or decompression therapy, spinal tension is typically maintained for periods of 30 minutes or longer.

As the spine is placed into a state of tension, the spinal vertebrae will occur morphology change, this requires the control system must have the dynamic positioning correction function. Meanwhile, the dynamic automatic positioning correction processing also allows the lesioned intervertebral disc time to heal in the non-loaded state. Additionally, herniated discs (nucleus pulposa) is produced in back to normal position via negative pressure created by the separation of the vertebrae, realized the intervertebral disc disease to accept reset. Meanwhile, This dynamic positioning correction function can also be aided to implement paraspinal muscles maximum relax according to the patient weight set nonlinear logarithmic minus pressure control system. Since the conscious human (patient) may voluntarily and/or subconsciously flex the spinal muscles in reaction to tensile forces. Either or both patient reactions degrade the effectiveness of spinal traction or spinal decompression therapy.

A common spinal decompression therapy utilizes a non-feedback-providing tension producing actuator (any type of electro-mechanical, pneumatic, magnetic, hydraulic, or chemical actuator) connected to a patient via a patient interface device. The patient lay supine upon a treatment bed, head distal to the applied tension source. An upper body patient harness secures the upper patient body to the distal end of the bed (that end of the bed furthest from the source of tensile force generation). A lower body harness secures about the waist, and serves as the point at which the tension strap is connected. Tension-producing actuator output is increased or decreased to produce resultant tension changes at the point where the strap is attached to the patient. A linear actuator (any type of electro-mechanical, pneumatic, magnetic, hydraulic, or chemical actuator) is utilized to pull the patient's whole spine. And spinal decompression treatment system is based on the weighing data system by weighing the patients, for patients to be automatic setting decompression treatment, through the imaging data combining with a narrative, healthcare provider will complete lesions of the initial position, the positioner raise and lower the point at which the tension strap pulls from (treatment positioner), relative to the place of attachment to the patient, thus adjusting the angle of applied tension. The system also includes a tension measuring device (e.g., a loadcell) that is connected inline with the tension-producing actuator and patient to communicate tension metrics to a tension-producing actuator controlling device (e.g. computer). Thus, the system operates as a controlled-feedback loop whereby a planned tension profile can be applied to the patient and the actual applied forces can be verified by the computer.

In the above example, the point at which the tension strap pulls from relative to the place of attachment to the patient is typically fixed during application of tension. As the direction of pull is neither parallel nor perpendicular to the patient's spine, and as the patient lay supine (in this example) with their head distal to the applied tension source, the applied tension can be modeled as two force vectors, one inline with the patient's spine and away from the head, and one perpendicular to the patient's spine. In the event that the patient lay prone, the direction of the horizontal component of the applied tension resultant would remain the same, however the direction of the vertical component of the applied tension resultant would be reversed.

One defining characteristic of spinal decompression is that tension is applied at an angle, and that specific angles (which are specific to each device's design) affect a specific positioning ability to allow healthcare providers to treat location specific injuries, such as herniated spinal discs. In effect, locating the site(s) of spinal elongation maximizes the therapeutic benefit per therapy session. Traction, whereby forces are applied mostly inline with the spine, does not attempt to maximize spinal discs at specific interdiscal locations and spinal elongation position column by the adjustment on the angle of tension in spinal.

Devices of the type described above provide general guidelines as to the relative interdiscal space(s) affected by various angles of applied tension. These angles are calculated in many ways; no standards exist for their calculation. Spinal decompression manufacturers calculate which interdiscal space(s) is affected by relating applied tension force vectors (specific to their device) to commonly available radiographical charts. These radiographical charts typically show the 'average spine' (based on studies of measurements taken over many patients) or the 'ideal spine' (based on best-fit mathematical modeling of the spine). Variations in patient's spines can mean that a treatment angle designed to align the L4 and L5 vertebra actually is insufficient to align said vertebra or overly much, brining inferior vertebra in-line with unintended superior vertebra.

The shape of the human spine varies from human to human. Lordosis, or an inward curve (towards the front of the patient body), and kyphosis, or an outward curve (towards the back of the patient body), exist throughout the spine, and serve to balance the spine and body. Generally, the spine exhibits a lordotic curve between the Thoracic (middle spine) and Lumbar (lower spine) regions, and a kyphotic curve between the Thoracic and Cervical (upper spine or neck) region. The points and degree of inflection and deflection vary across patient populations.

At present, Magnetic Resonance Imaging (MRI) is routinely indicated prior to spinal decompression therapy, whereby affected disc levels are identified. Once the MRI-described interdiscal space(s) is established, healthcare providers follow spinal decompression device manufacturer's recommendations as to appropriate applied tension treatment angles. The healthcare provider is able to judge, by physical examination of the patient, advanced patient imaging (MRI, CT, X-ray, etc.), spinal decompression device manufacturer's treatment angle design, and experience using spinal decompression devices the 'most likely' proper treatment angle for a particular patient. Once the patient is actually on the spinal decompression device, strapped in, the final level of scrutiny by the healthcare provider with regards to treatment angle occurs. The healthcare provider will visually observe the patient's posture, feel the patient's spine and or other related bodies, and/or query the patient to make a final determination as to the correct treatment angle for that particular patient.

At present, The spinal pressure relief devices are employed angle positioning technology, healthcare providers must do one of two things when adjusting treatment angle after initiating treatment. The first option, pausing treatment, adjust treatment angle, and restart treatment, but since the provider can't dynamic continuous real-time observation of the spine in the minus pressure condition of the patients with feedback in this case, thus even if to adjust, can not ensure the accurate angle, which makes it difficult to realize patients and the provider interactive communication, scanning, and ultimately positioning lesions in the purpose of the position. The second option, in the treatment process and under the action of tension, while the provider observes and adjusts the angle. But this practice, since human operation, will inevitably change dynamic system in the system, which leads to exceed expected tension setting range change. This adjustment, for the present not tension compensation of the closed loop feedback system (with tension compensation feedback closed-loop system can make the expected tension in a time constant), due to the sudden change of angle, will make the expected tension suddenly changes that lead to spinal side muscle strong contraction, thus affecting the treatment effect.

The present invention seeks to demonstrate a unique method for fine tuning treatment angle for each patient. The present invention proposes a system designed to allow the healthcare provider to adjust treatment angle without changing intended tension levels. The system proposed would be able to account for mechanical dynamics and mechanical advantages of the system, and be calibrated to anticipate the increases and decreases in resultant tension that would otherwise occur while changing treatment angle under tension.

BRIEF SUMMARY OF THE INVENTION

The present invention relates to a tension producing actuator feedback and correction system. The system is fast enough to allow treatment angle change under tension without changing intended tension, the advantages of this design are numerous. While the patient is under an initial intended tension and treatment angle, the healthcare provider can observe via sight and touch, and additionally querying the patient, the interdiscal sites affected by the initial treatment angle at which the resultant tension is applied to the patient. Keeping the patient at the initial intended tension while changing treatment angle (without changing intended tension level) allows the healthcare provider to observe, via at least the same pathways, the transition in patient posture, without inciting paraspinal muscle contraction due to unintended tension level changes. Dynamically adjusting treatment angle under tension allows the healthcare provider to adjust, up or down, the treatment angle to accommodate increases and decreases in lordosis, as observed under tension. Dynamically adjusting treatment angle under tension also allows the healthcare provider to query the patient for comfort and or increases or decreases in perceived pain, incorporating a measure of biofeedback into the therapy.

In general, the patient is positioned supine on the treatment bed, their lower spine over a lordotic support. The lordotic support is used to locate the apex of lordosis, which is utilized as a universal metric for calculating treatment angle across average or ideal patient morphologies. Regardless of the design of treatment angles for a specific spinal decompression or traction device, the device does include treatment angle designations designed to affect specific interdiscal locations. While the inclusion of designer treatment angle designations for a spinal decompression or traction device is not required, it is likely present per the current technology.

Average or ideal radiographical spinal models typically include a mean segmental angle and at least the first or second standard deviation measurements. The segmental angle would be an angle of lordosis, in the case of the lumbar spine, between one or more vertebra. The segmental angles utilized would be those between the fifth lumbar vertebra and the first sacral vertebra or L5-S1, the fourth and the fifth lumbar vertebra or L4-L5, the third and the fourth lumbar vertebra or L3-L4, the second and the third lumbar vertebra or L2-L3, and the first and second lumbar vertebra or L1-L2.

The design of the spinal decompression device provides treatment angles which would align vertebra (spinal disc) and elongate their intervertebral spaces for an average or ideal spine. As described above, differences in the degree of lordosis between vertebral segments will range slightly above or below the average or ideal models.

If the spinal decompression device is designed to allow treatment angle change without changing intended tension, and that treatment angle change is bounded by one standard deviation of measured or calculated (depending on the data used in the design of the device), then the device is capable of accommodating the average or ideal spine and all those patients within one standard deviation of the average or ideal model, formed according to an embodiment of the present invention. The device's dynamic angle adjustment bounds may be extended to two or even three standard deviations of the average or ideal model, to accommodate even more patients. The device's dynamic angle adjustment bounds may incorporate the entire angle adjustment range of the device, allowing the healthcare provider to move up and down the entire lower spine.

By first utilizing angles described by spinal decompression device manufacturers as treating specific interdiscal locations and by then applying tension at that angle, the healthcare provider is able to initiate therapy in the general location of the interdiscal space(s) to be treated. If the healthcare provider is then capable of further adjusting the angle of applied tension during the application of said tension, and if the tension feedback and correction mechanism of the spinal decompression device is fast and accurate enough such that no noticeable increase or decrease in intended tension is incurred (thus minimizing conscious and subconscious paraspinal muscle contraction), the healthcare provider is then capable of fine tuning the treatment angle. The healthcare provider can observe real-time changes in the patient and the alignment of their spine, under tension. Paraspinal muscles may contract in response to stretching, and definitely will contract in an involuntary guarding response if sudden changes in tension occur. If the spinal decompression device's tension control feedback and correction loop is fast and accurate enough to allow for angle change and compensate for inevitable changes in mechanical advantage such that the paraspinal muscles are not incited to guard and contract, then the healthcare provider can in effect 'scan' the patient's spine in the vicinity of the interdiscal space(s) of interest. This process may be limited to an initial period of treatment. This process may also be limited to a range of angle adjustment, whereby the healthcare provider selects an initial treatment angle based on diagnostic evidence and device manufacturer design, and then fine tunes only to less than, only to greater than, or above and below the initial treatment angle by a certain amount (e.g., 0.5 degrees).

In summary, the present invention describes the device of which as being capable of adjusting the angle of applied tension without changing (significantly) the amount of intended tension, such that the healthcare provider can adjust the angle of tension during the application of tension without inciting conscious or subconscious paraspinal muscle contraction.

Additionally, the present invention may be utilized in conjunction with patient feedback to help locate the treatment angle that best addresses the patient's pain. Just as therapeutic massage addresses muscular tensions, whereupon the recipient of the massage knows instantly when the therapist addresses the correct site or source of pain, so may the patient undergoing spinal decompression therapy recognize when a spinal decompression device addresses the correct interdiscal site or source of pain. If the healthcare provider is then capable of further adjusting the angle of applied tension during the application of said tension, and if the tension feedback and correction mechanism of the spinal decompression device is fast and accurate enough such that no noticeable increase or decrease in intended tension is incurred, the healthcare provider is then capable of querying the patient real-time as to whether increasing or decreasing the angle of applied tension feels more or less appropriate. By scanning the spine and querying the patient as to what feels more appropriate, the healthcare provider has an additional input as to the correct location for spinal decompression to be maximized.

According to one respect of the present invention, providing a tensioning device, comprising: a patient-positioning means configured to high precisionly, repeatedly align a target region of a patient spine; a tension-producing actuator configured to place a patient spine in tension; a positioning device operationally configured to position tension producing actuator relative to target region of patient spine; a patient interface device operationally configured to interface tension producing actuator with patient spine; a control system with feedback on resultant tension vector applied to patient spine operationally configured to allow for adjustment of either tension producing actuator position, patient position, or both while applying tension to the patient spine during non-therapeutic tension levels; and a display operationally configured to provide data regarding resultant tension vector to the user or healthcare provider; wherein the control system automatically adjusts tension producing actuator work levels such that resultant tension vector magnitude remains ideally constant during adjustment of resultant tension vector angle, reducing risk of eliciting paraspinal muscle contraction due to changes in resultant tension vector magnitude.

The patient positioning means includes a patient bed, wherein a region of the patient bed is identified as the alignment-region over which a target region of the patient spine should be positioned. The patient bed includes physically removable portions of the bed body and a series of physical device related to the treatment attached thereof.

The tension producing actuator includes an electro-mechanical device which generates torque through rotation. The tension producing actuator includes a means of increasing or decreasing torque generated.

The positioning device includes a removable positioning means by which increases and decreases in the height of the tension producing actuator relative to the target region of the patient spine are accomplished.

The patient interface includes a strap connected to a patient harness, one end of the strap includes a connection to the rotation of the tension producing actuator, and a connection to a patient harness at its opposite end, the patient harness cradling a portion of the patient pelvis and the spine. The patient interface is operationally configured to translate the decompression tension generated by the torque generated by the tension producing actuator to the patient spine.

The control system allows for user or healthcare provider input and includes a means to set, generate, and keep ideally constant resultant tension vector magnitude during which either resultant tension vector angle or patient spine target region position relative on the device is adjusted by user or healthcare provider. The control system allows for user or healthcare provider to modify resultant tension vector angle while tension is applied to patient spine, the resultant tension vector magnitude kept ideally constant, while patient spine target region position relative to a location on the device is unchanged.

The control system allows for user or healthcare provider to modify patient spine target region position relative to a location on the device while tension is applied to patient spine, the resultant tension vector magnitude kept ideally constant, while tension producing actuator position relative to a location on the device is unchanged.

The control system allows for user or healthcare provider to set resultant tension vector angle and to modify patient spine target region position relative to a location on the device while tension is applied to patient spine, the resultant tension vector magnitude kept ideally constant, the control system automatically adjusting tension producing actuator position relative to a location on the device to maintain user set resultant tension vector angle.

The control system includes a display or means for communicating resultant tension vector angle and magnitude to the user or healthcare provider.

The control system allows for a user or healthcare provider to visually assess, physical palpitate, or verbally or otherwise receive feedback from the patient to modify patient position and to achieve concentration of resultant tension vector magnitude near a vertebral area of interest during applied ideally constant resultant tension vector magnitude.

The control system indicates the region of the spine where resultant tension is concentrated based on empirical calculation of said location relative to a spinal model and mathematical and medical assumptions.

The control system calculates region of the spine where resultant tension is concentrated based on ideal spine models arrived at through clinically cited spinal morphology studies.

The user or healthcare provider is able to visually assess, palpitate, and/or query patient to determine optimum pretreatment treatment angle or resultant tension vector angle while reducing risk associated with eliciting a paraspinal muscle contraction due to changes in resultant tension vector magnitude.

Figure 1:
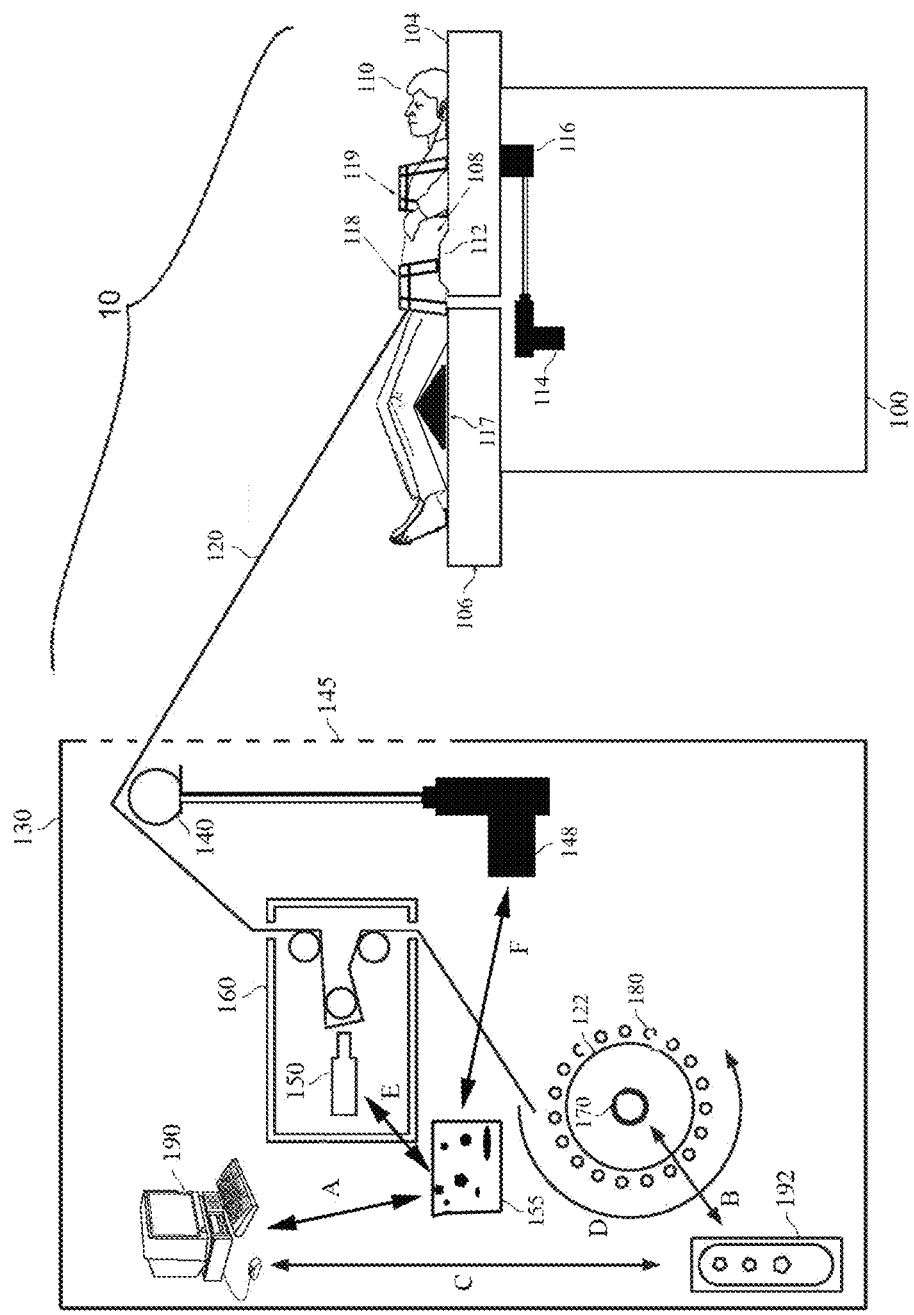
FIG. 1 illustrates a side view of a spinal therapy system formed according to an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION OF THE INVENTION

FIG. 1 illustrates a spinal therapy system 10 used to treat a patient 110 formed according to an embodiment of the present invention. The system 10 includes a microprocessor, control system, or computing device 190 having firmware and/or software that operates to utilize and control an actuator 170. The computing device 190 is configured to interface with a user, such as by use of a monitor and keyboard setup. By way of example only, the actuator 170 may be electronically, hydraulically, pneumatically, or mechanically operated. The actuator 170 is connected to a patient 110 via a patient interface device 120. By way of example, the actuator 170 may be operated through a system of gears or pulleys such that the tensile forces applied to the patient 110 by the patient interface device 120 are carefully controlled. This system 10 is used to perform decompression therapy on the patient 110 by applying cycles of tensile forces from the actuator 170 on the spine 108 of the patient 110 through the interface device 120. Alternatively, the system 10 may be used to perform traction therapy without use of cycles of tensile forces.

The patient 110 is positioned supine on a mechanical apparatus 100 that may be a flat surface such as a bed or table. The bed 100 includes a head end 104 where the patient 110 lay his or her head and a base end 106 where the patient 110 lay his or her legs and feet. The bed 100 is positioned such that the patient 110 may be easily placed into alignment for treatment with the system 10. Additionally, the bed 100 may employ arm supports or rails to position the patient 110. The patient 110 wears a lower-body harness 118 that is connectable to the patient interface device 120. This lower-body harness allows for connection to the patient interface device 120 at or near the base of the sacrum, or is designed to locate the origin of the resultant tension vector at or near the base of the sacrum. Alternatively, the patient may wear any other appropriate device that is configured to connect the patient 110 to the interface device 120, provided the device position the origin or locate the origin of the resultant tension vector at or near the base of the sacrum. The patient 110 wears an upper-body harness 119 that is connectable to the head end 104 of the bed 100. The upper-body harness 119 secures the upper body of the patient 110 to the bed 100, and keeps the upper body of the patient 110 from moving towards or away from the tower 130 which houses the actuator 170 and interface positioning device 140.

The healthcare provider positions the patient's 110 lumbar spine 108 over an adjustable lordotic support 112. The adjustable lordotic support 112 is pneumatically inflated and deflated to accommodate various degrees of lumbar lordosis between patients 110. The lordotic support 112 may be adjustable or fixed in shape, and may be adjustable by several methods, including pneumatic, electro-mechanical, hydraulic, chemical, etc. Specifically, the healthcare provider positions the apex of lordosis, the third lumbar vertebra (L3), over the center-top of the lordotic support 112. Positioning the apex of lordosis over the center-top of the lordotic support 112 and anchoring the patient's 110 upper body to the head end 104 of the bed 100 forms a reliable and consistent endpoint for the horizontal line (opposite side) of the triangle which is used to calculate treatment angle.

The healthcare provider places a knee bolster 117 under the patient's 110 knees, reducing pressure on the patient's 110 lower spine 108. The patient's 110 position on the bed 100, supine with a bolster 117 under the knees, forms the basis for selection of radiographical measurements which take into account this position for use in designating treatment angles.

The lower-body harness 118 is connected to the actuator 170 by the patient interface device 120. The harness 118 may be connected to the patient interface device 120 through a clip or buckle that may alternately be secured and removed. The interface device 120 is configured to deliver and align tensile forces generated by the actuator 170 through the harness 118 along the spine 108 of the patient 110.

The interface device 120 may be a strap, belt, or cable that is positioned relative to the patient 110 via a patient interface positioning device 140. The patient interface positioning device 140 may itself be moved to preferred positions by an vertical actuator 148, which may be a linear actuator, or any other type of electro-mechanical, pneumatic, hydraulic, or chemical actuator. The vertical actuator 148 may contain a relative or absolute encoder, potentiometer, or optical distance sensor, for use in communicating the position of the patient interface positioning device 140 to an electronic communication hub 155 by way of arrow F. The patient interface device 120, as it travels up and down via the patient interface positioning device 140 and vertical actuator 148, may pass thru a slot 145 in the front of the tower 130, which may utilize some form of flexible material to move with the patient interface device 120 and shield the inside of the tower 130 from outside interference.

The head end 104 and base end 106 bed 100 mattresses may be moved together horizontally towards and away from the tower 130 via a horizontal actuator 114 and clevis 116, which may be a linear actuator or any of electro-mechanical, pneumatic, hydraulic, or chemical type. This would generally be done to accommodate patients 110 of various heights, such that those patient's 110 feet would not be uncomfortably near to or beyond the base end 106 of the bed 100. The horizontal actuator 114 may contain a relative or absolute encoder, potentiometer, or optical distance sensor, for use in communicating the position of the lordotic support 112 and head end 104 mattress to either or both the computing device 190 and electronic communication hub 155.

The base end 106 mattress of the bed 100 is designed to be locked into place with and travel horizontally with the head end 104 mattress of the bed 100. It is also capable of unlocking from the head end 104 mattress of the bed 100, and traveling a fixed distance away from the head end 104 mattress of the bed 100 along linear guides. This function serves to allow the spine 108 to elongate more easily under tension, as opposed to slipping and sliding down the base end 106 mattress of the bed 100 were it fixed to the head end 104 mattress. The base end 106 mattress and head end 104 mattress were joined entirety, this case would be less favorable for the spine free elongation with the decompression tension.

The system 10 further includes a tensile force feedback system 160 which engages the interface device 120 between the actuator 170 and the lower-body harness 118. The feedback system 160 may include a loadcell or dynamometer 150 that is positioned inline with the actuator 170 and is configured for electronically providing feedback to the electronic communication hub 155 as indicated by arrow E.

The electronic communications hub 155 is designed to collect and relay various system 10 metrics to the computing device 190 as indicated by arrow A. This device may synchronize various system 10 measurement device information into a single data stream A designed to be best utilized by the computing device 190.

The actuator 170 electronically communicates with, and is controlled directly by, an actuator controller 192 as shown by arrow B. By way of example only the actuator controller 192 is a servo-amplifier 192. The actuator 170 may also be attached to, or connected inline with, an encoder 180 that is capable of communicating motor shaft position and other motor metrics with the servo-amplifier 192. The servo-amplifier 192 may be capable of calculating any number of motor metrics, including work, position, distance, torque, and rate and electronically communicating those metrics to, and receiving them from, the computing device 190 as indicated by arrow C to the computing device 190.

The computing device 190 may be configured to communicate with the servo-amplifier 192, and the actuator 170, to monitor and to correct as needed the resultant tensile force and motor metrics applied by the actuator 170 from the servo-amplifier 192. The computing device 190 may also be configured for use with a user interface system (e.g., keyboard and monitor) which communicates and deciphers the user's commands to the computer 190. This interface allows the user to structure treatment parameters. By way of example, all tension-producing and delivery apparatus are contained within a tower 130 located in a position relative to the patient 110.

In operation, spinal treatment begins by positioning the patient 110 correctly onto the bed 100. The patient's head is positioned at the head end 104 of the bed 100, and the patient's feet are positioned at the base end 106 of the bed 100. The patient 110 is outfitted with the lower body harness 118 such that the patient 110 is connected to the patient interface device 120, and the lower body harness 118 is configured to apply tensile forces to the spine 108 of the patient 110, the origin of the resultant tension vector located at or near the base of the sacrum. The patient is outfitted with an upper body harness 119 which is fixed into position at the head end 104 of the bed 100. The healthcare provider positions the patient's 110 apex of lordosis over the center-top of the lordotic support 112, adjusts the height of the support to match the curvature of the patient's lordosis there, and adjusts the upper-body harness 119 connection to the head end 104 of the bed 100 to make certain the upper body of the patient 110 is fixed into position on the head end 104 mattress. A bolster 117 is placed under the patient's 110 knees.

The operator of the decompression system 10 may use the patient interface system of the computer 190 to select the proper treatment parameters for the therapy. The operator may then select a tension treatment program for the patient 110 and instruct the computing device 190 to execute the selected treatment profile. The computing device 190 activates the servo-amplifier 192 and/or actuator 170 such that the actuator 170 rotates, for example in the direction of arrow D, to tighten the patient interface device 120 and thus apply tension to the patient's spine 108 through the lower body harness 118. The computing device 190 adjusts the tensile output to follow the cycles of tensile forces defined in the treatment program entered by the user. The program may include low and high tension plateaus above, by way of example only, 125 pounds, and may also include any number of decompression therapy variations cyclically applying tension to the patient's spine 108.

Figure 2:
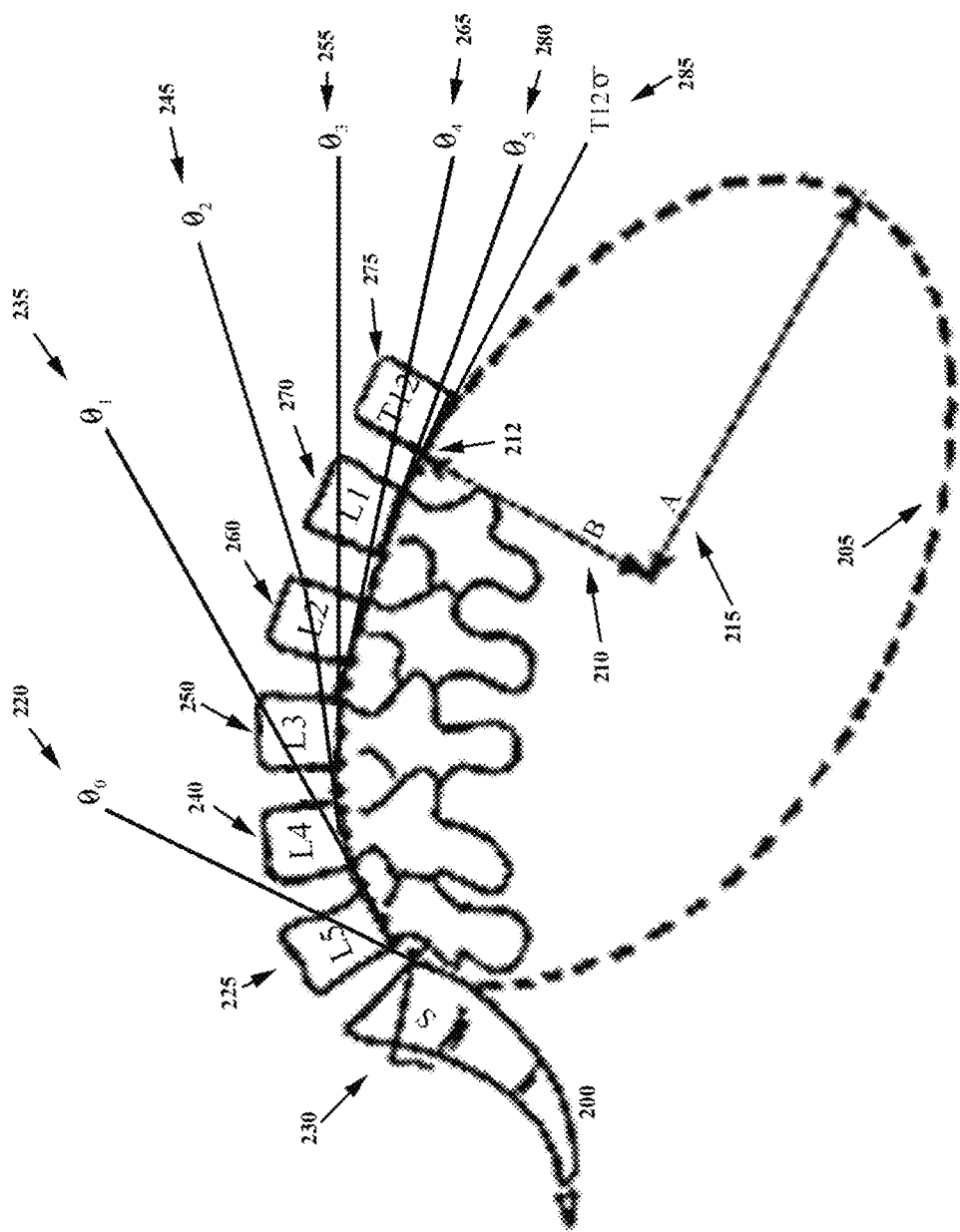
FIG. 2 illustrates the coccyx, sacrum, and lumbar spine, the lumbar spine being modeled about an ellipse, showing angles between adjacent vertebra.

FIG. 2 illustrates the Lumbar Lordosis Elliptical Model 205 formed of radiographic measurements over many patients. Janik et all developed an idealized average subject anthropometric model of the lumbar lordosis from inferior of T12 to superior S1. The elliptical model 205 represents the idealized path of the posterior longitudinal ligament along the posterior aspect of the vertebral bodies2. This model 205 represents one method by which spinal decompression device designers may designate treatment angles formed according to an embodiment of the present invention. The ellipse 205 about which the spine 200 is modeled has minor axis B 210 passing through the inferior endplate 212 of T12 275 and a major axis A 215 perpendicular to the minor axis 210 Janik et all found the b/a ratio of 0.32 to be the best fit for the data presented.

The lower spine 200 pictured in FIG. 2 is composed of the first sacral vertebra 230 (S1), the fifth lumbar vertebra 225 (L5), the fourth lumbar vertebra 240 (L4), the third lumbar vertebra 250 (L3), the second lumbar vertebra 260 (L2), the first lumbar vertebra 270 (L1), and the twelfth thoracic vertebra 275 (T12).

The tangent lines in FIG. 2 are drawn according to the Harrison Posterior Tangent (HPT) method. The HPT lines drawn along the posterior bodies of the bony vertebra are shown, the angle between adjacent tangent lines defining the segmental angle between vertebra per the elliptical model 205.

The segmental angle between L5 225 and S1 230, or L5-S1, is determined by the angle between the tangent lines $\theta_1$ 235 and $\theta_0$ 220.

The segmental angle between L4 240 and L5 225, or L4-L5, is determined by the angle between the tangent lines $\theta_2$ 245 and $\theta_1$ 235.

The segmental angle between L3 250 and L4 240, or L3-L4, is determined by the angle between the tangent lines $\theta_3$ 255 and $\theta_2$ 245.

The segmental angle between L2 260 and L3 250, or L2-L3, is determined by the angle between the tangent lines $\theta_4$ 265 and $\theta_3$ 255.

The segmental angle between L1 270 and L2 260, or L1-S2, is determined by the angle between the tangent lines $\theta_5$ 280 and $\theta_4$ 265.

The segmental angles discussed above are utilized according to an embodiment of the present invention to determine angles specific to the device of FIG. 1 for treating various portions of the lumbar spine 200. Different radiographical methods and data may be more or less appropriate for a specific spinal decompression device design. It is important to choose measurement data that befits the patient's 110 position on the device, in the system of 10 that being supine and with a bolster under the knees.

Figure 3:
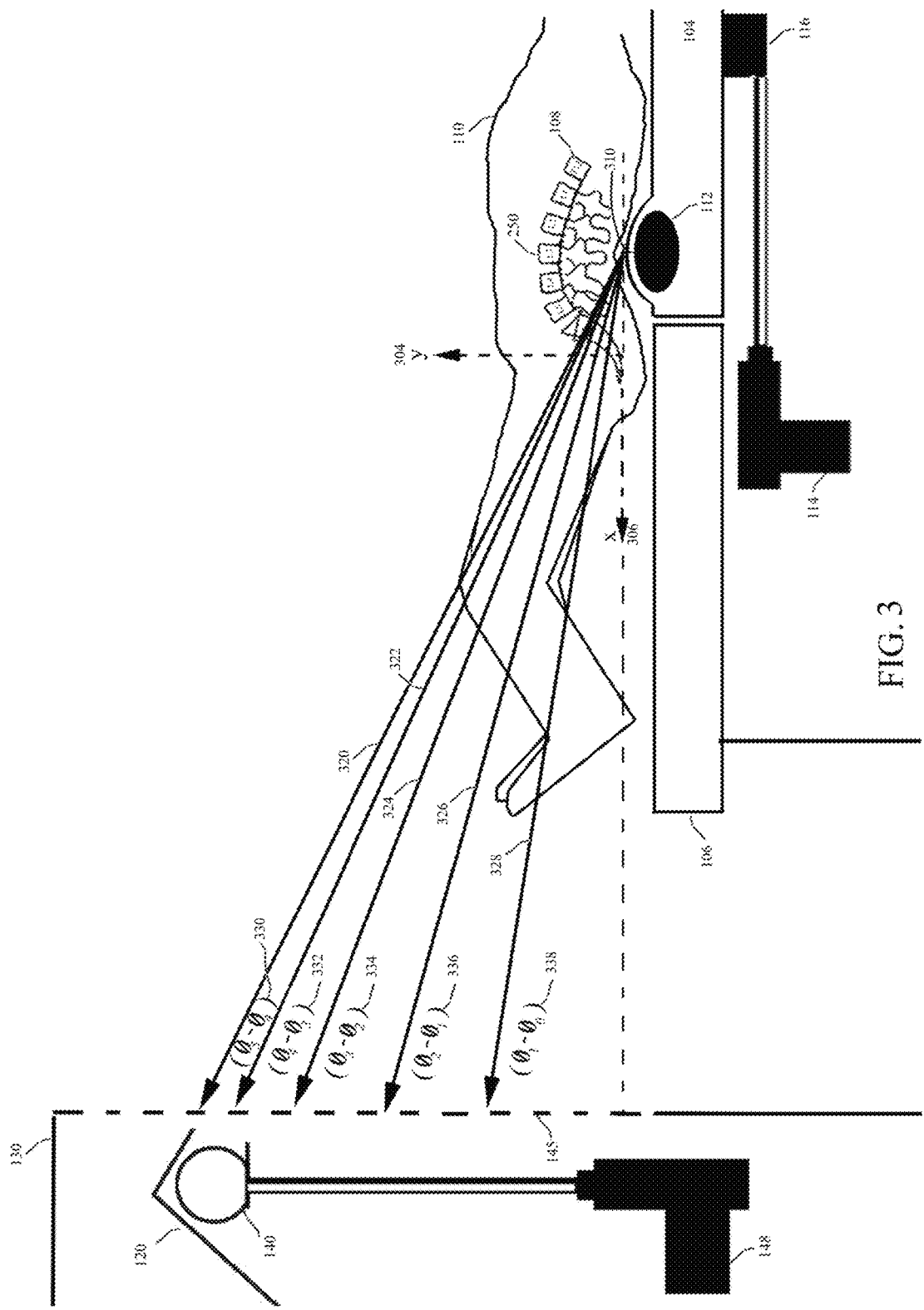
FIG. 3 illustrates a side view of a spinal therapy system utilizing a lordotic support, specific patient positioning, and treatment angle structure based on FIG. 2, formed according to an embodiment of the present invention.

FIG. 3 illustrates a side view of the system 10 formed by an embodiment of the present invention, detailing the designation of treatment angles. The patient 110 is positioned supine on the bed 100, head on the head end 104 of the bed. The patient's 110 spine 108 is shown over the lordotic support 112, the apex of lordosis L3 250 over the center-top of the lordotic support 112. Although not shown, the lower body harness 118 is present, as indicated by the vertical and horizontal components 304 and 306, 'x' and 'y' respectively, of the resultant tension vector with origin 302 at the base of the sacrum 230. Also not shown, the upper body harness 119 is affixed to the head end 104 of the bed 100. The bolster 117 is not shown; however the patient's 110 legs are angled as if over the bolster 117.

As the patient interface device 120 is retracted by the actuator 170, S1 230, by way of the lower body harness 118, is rotated upward. The apex of lordosis, L3 250 acts as the fulcrum 310 for this rotation, as S1 230, L5 225, and L4 240 all reside below L3 250. L3 250 acts to oppose the movement of S1 230 in the vertical direction 'y' 304 as L3 250 upon the lordotic support 112. This opposition continues until the treatment angle is sufficient to act upon the L3 250 vertebral body. As L3 250 is acted upon and lifted, so the fulcrum 310 shifts superior to L2 260. As L2 260 is acted upon by a sufficient treatment angle, so the fulcrum 310 shifts superior once again to L1 270. In all cases the fulcrum 310 is formed by the opposition to an increase in treatment angle and more specifically to the vertical component of the resultant tension 'y' 304 against the lordotic support 112.

The hypotenuse 328 is formed of the patient interface device 120 at the point where it exits the tower 130 through slot 145 and the point 310. The treatment angle 338 is equivalent to the angle formed by the HPT lines 235 and 220 formed of the posterior sides of S1 230 and L5 225, ($\theta_1$-$\theta_0$) 338 or L5-S1

The hypotenuse 326 is formed of the patient interface device 120 at the point where it exits the tower 130 through slot 145 and the point 310. The treatment angle 336 is equivalent to the angle formed by the HPT lines 245 and 235 formed of the posterior sides of L5 225 and L4 240, ($\theta_2$-$\theta_1$) 336 or L4-L5. The entire treatment angle however would consist of ($\theta_2$-$\theta_1$) 336+($\theta_1$-$\theta_0$) 338.

The hypotenuse 324 is formed of the patient interface device 120 at the point where it exits the tower 130 through slot 145 and the point 310. The treatment angle 334 is equivalent to the angle formed by the HPT lines 255 and 245 formed of the posterior sides of L4 240 and L3 250, ($\theta_3$-$\theta_2$) 334 or L3-L4. The entire treatment angle however would consist of ($\theta_3$-$\theta_2$) 334+($\theta_2$-$\theta_1$) 336+($\theta_1$-$\theta_0$) 338.

The hypotenuse 322 is formed of the patient interface device 120 at the point where it exits the tower 130 through slot 145 and the point 310. The treatment angle 332 is equivalent to the angle formed by the HPT lines 265 and 255 formed of the posterior sides of L3 250 and L2 260, ($\theta_4$-$\theta_3$) 332 or L2-L3. The entire treatment angle however would consist of ($\theta_4$-$\theta_3$) 332+($\theta_3$-$\theta_2$) 334+($\theta_2$-$\theta_1$) 336+($\theta_1$-$\theta_0$) 338.

The hypotenuse 320 is formed of the patient interface device 120 at the point where it exits the tower 130 through slot 145 and the point 310. The treatment angle 330 is equivalent to the angle formed by the HPT lines 280 and 265 formed of the posterior sides of L2 260 and L1 270, ($\theta_5$-$\theta_4$) 330 or L1-L2. The entire treatment angle however would consist of ($\theta_5$-$\theta_4$) 330+($\theta_4$-$\theta_3$) 332+($\theta_3$-$\theta_2$) 334+($\theta_2$-$\theta_1$) 336+($\theta_1$-$\theta_0$) 338.

The patient interface device 120 and interface positioning device 140 is raised and lowered by the vertical actuator 148 to accommodate the various designated treatment angles 320, 322, 324, 326, and 328. The system 10 utilizes passive or absolute encoder, potentiometer, optical distance sensor, or other distance metering feedback to determine vertical position of the patient interface device 120. The bed 100, composed of the base end 106 mattress and head end 104 mattress, is moved together horizontally towards and away from the tower 130 via the horizontal actuator 114. The position of the horizontal actuator 114 is known to the system 10 via passive or absolute encoder, potentiometer, optical distance sensor or other distance metering feedback. Together, the vertical position of the patient interface device 120 at the interface positioning device and the horizontal position of the center-top 310 of the lordotic support 112 via the horizontal actuator 114 are known to the system and are used to calculate treatment angle.

Figure 4A:
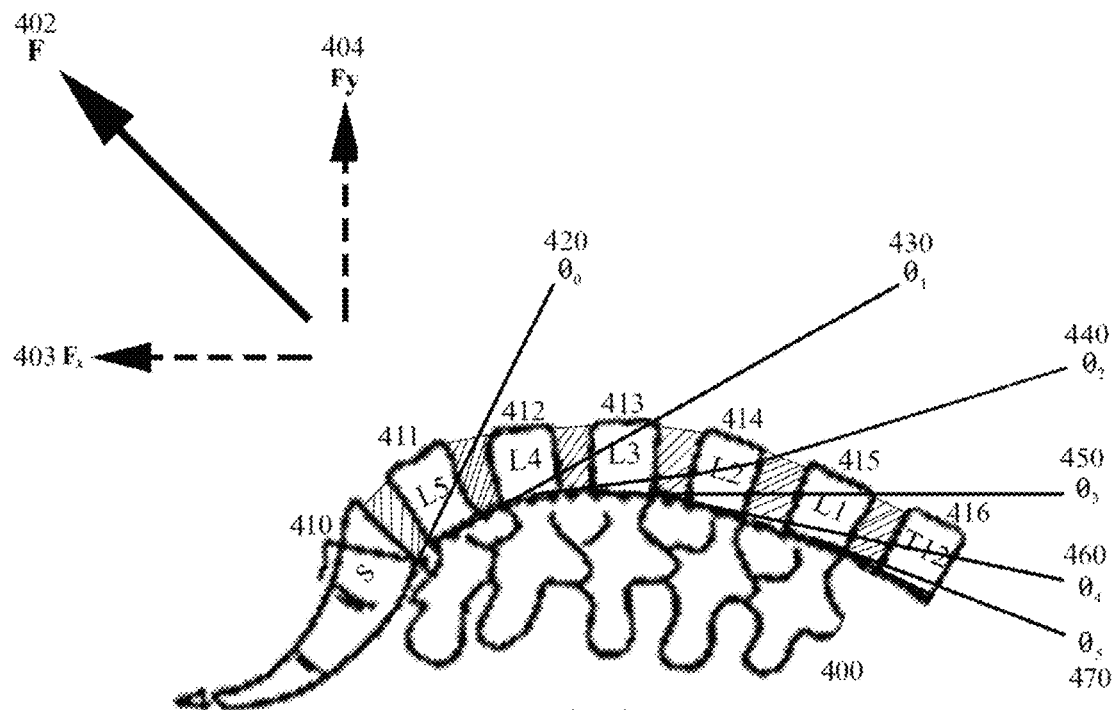
FIGS. 4A and 4B illustrate two side views of a coccyx, sacrum, and lumbar spine before and after the application of tension at a specific angle designed to align the sacrum and lowest lumbar vertebra (S1 and L5 respectively) and to elongate that interdiscal space (L5-S1), formed according to an embodiment of the present invention.
Figure 4B:
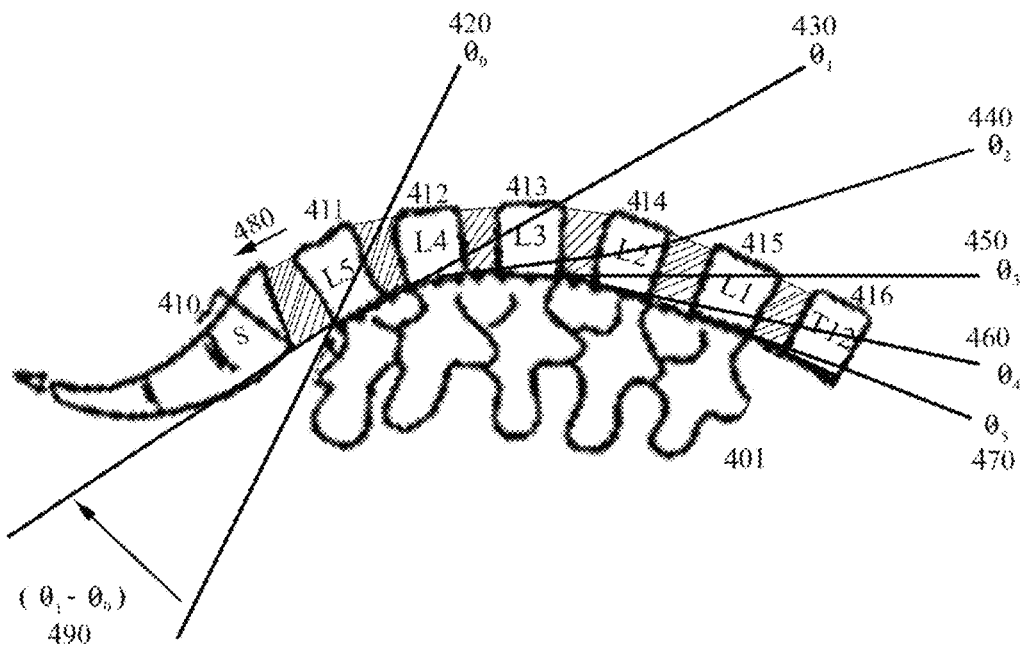

FIGS. 4A and 4B contain two views of the lower spine, 400 and 401. The upper view of FIG. 4A, 400, illustrates the spine before the additional application of resultant tension vector F 402 at treatment angle 490. The lower view of FIG. 4B, 401, illustrates the spine after application of said resultant F 402.

The HPT tangent lines 420, 430, 440, 450, 460, and 470 are drawn posterior to the vertebral bodies S1 410, L5 411, L4 412, L3 413, L2 414, and L1 415.

The resultant F 402 is applied to the patient 110 via the patient interface device 120 via the lower body harness 118. The lower patient harness 118 is designed to originate the resultant tension vector F 402 at the base of the sacrum 410, underneath the supine patient 110 in this embodiment of the present invention. The resultant F 402, when broken down into a vertical Fy and horizontal Fx component 404 and 403, acts in two ways on the lower spine 400/401. First, the vertical component Fy 404 can be thought of as lifting, from the sacrum 410, countered by the third vertebra L3 413, the apex of lordosis, upon the center-top 310 of the lordotic support 112. The horizontal component Fx 403 can be thought of as pulling through the aligned spinal segments to elongate the spine.

In 400, none of the spinal segments 410, 411, 412, 413, 414, 415, and 416 have a segmental angle of zero (aligned) as there are no external forces acting on the spine and it is assumed some amount of lordosis is naturally present in between all segments of the lower spine in the patient. Were there no natural lordosis whatsoever in the lower spine 400, and simultaneously no natural kyphosis, then there would be no need to utilize any treatment angle other than zero degrees.

The lower spine in 401 is acted upon by the resultant 402. The vertebral segment S1 410 is acted upon via the resultant 402 via the lower body harness 118 via the patient interface device 120. The magnitude of the resultant tension 402 is set as a general guideline to ½ patient body weight as is customary in the art; however the healthcare provider is responsible for tuning this magnitude sufficient to lift the lower and rotate the lower patient body, sacrum/pelvis/hips, into position. The vertebral segment S1 410 is caused to lift and rotate relative to the inferior endplate of L5 411 per the vertical component Fy 404 of resultant tension 402. The angle of application 490 of resultant tension 402 is $\theta_1$-$\theta_0$, 430-420, which is sufficient to bring the posterior sides of the vertebral bodies S1 410 and L5 411 parallel to each other, and so into 'alignment'. Once the vertebral bodies S1 410 and L5 411 are aligned, the intervertebral discs are decompressed uniformly 480, anterior and posterior. Through the cycling of resultant tension 402, between maximal and minimal levels, the vertebral bodies S1 410 and L5 411 are brought into and out of alignment.

The bringing of into and out of alignment of the vertebral bodies S1 410 and L5 411 results in a confusion and relaxation of paraspinal muscles, especially when resultant tension 402 is cycled smoothly. Additionally, the bringing of into and out of alignment of the vertebral bodies S1 410 and L5 411 results in increased imbibition by the intervertebral discs at the end plates of the vertebral bodies, as the process by which imbibition occurs is a mechanical movement of vertebral bodies relative to each other, as described by the bringing into and out of alignment of said bodies. Further, the elongation 480 of aligned vertebral bodies S1 410 and L5 411 results in a drop in interdiscal pressure at the location of elongation, which acts to move nucleosus pulposus through the spine.

Figure 5A:
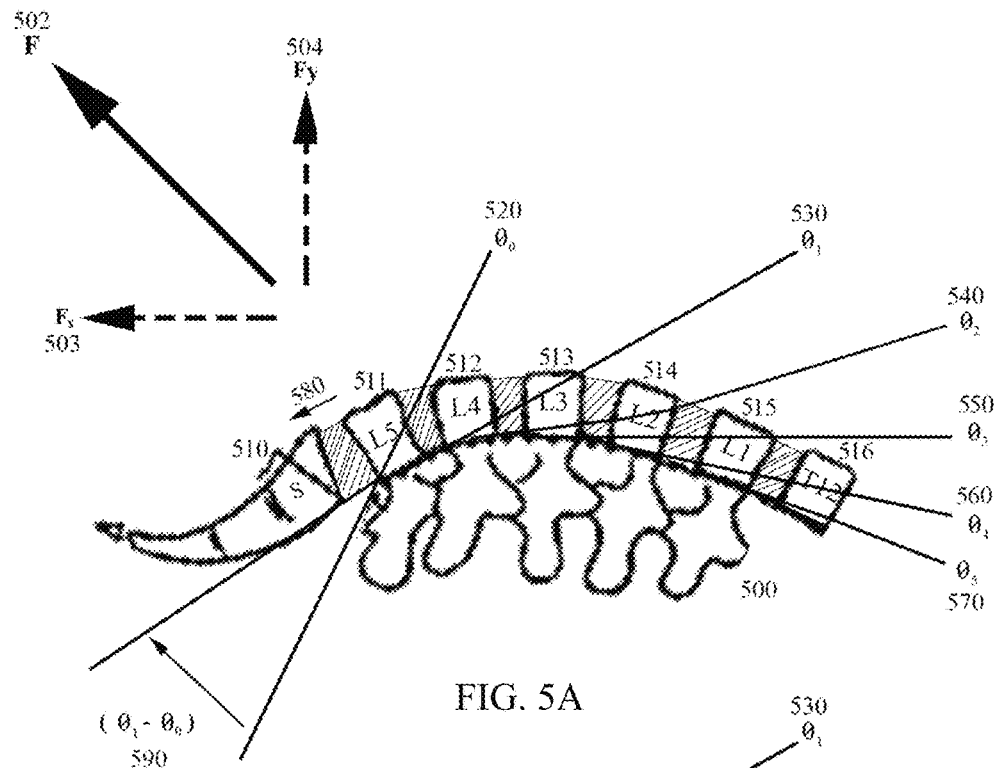
FIGS. 5A and 5B illustrates two side views of a coccyx, sacrum, and lumbar spine. The upper view illustrates the lower spine after the application of tension at an angle designed to align the sacrum and lowest lumbar vertebra (S1 and L5 respectively) and to elongate that interdiscal space (L5-S1). The lower view illustrates the upper view after the application of tension at an additional specific angle designed to align the lowest lumbar vertebra with the fourth distal lumbar vertebra (L5 and L4 respectively), and to elongate the interdiscal spaces (L5-S1 and L4-L5), formed according to an embodiment of the present invention.
Figure 5B:
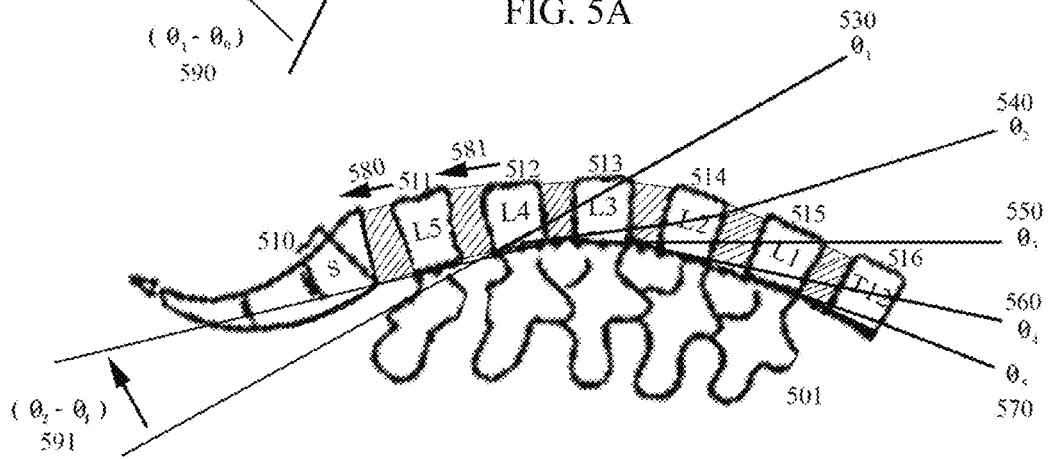

FIGS. 5A and 5B contain two views of the lower spine, 500 and 501. The upper view of FIG. 5A, 500, illustrates the spine before the additional application of resultant tension vector F 502 at treatment angle 591. The upper view of 500 is analogous to the lower view 401 of FIG. 4B, rotated by 490 and elongated 480. The lower view of FIG. 5B, 501, illustrates the spine after application of said resultant F 502.

The HPT tangent lines 530, 540, 550, 560, and 570 are drawn posterior to the vertebral bodies L5 511, L4 512, L3 513, L2 514, and L1 515.

The resultant F 502 is applied to the patient 110 via the patient interface device 120 via the lower body harness 118. The lower patient harness 118 is designed to originate the resultant tension vector F 502 at the base of the sacrum 510, underneath the supine patient 110 in this embodiment of the present invention. The resultant F 502, when broken down into a vertical Fy and horizontal Fx component 504 and 503, acts in two ways on the lower spine 500/501. First, the vertical component Fy 504 can be thought of as lifting, from the sacrum 510, countered by the third vertebra L3 513, the apex of lordosis, upon the center-top 310 of the lordotic support 112. The horizontal component Fx 503 can be thought of as pulling through the aligned spinal segments to elongate the spine.

In 500, only S1 510 and L5 511 are aligned, as described in 401 of FIG. 4B. None of the other spinal segments 511, 512, 513, 514, 515, and 516 have a segmental angle of zero (aligned) as the resultant 402 acting on the spine is at a treatment angle sufficient only to align 510 and 511. Additionally, it is assumed some amount of lordosis is naturally present in between all segments of the lower spine in the patient 110. Were there no natural lordosis whatsoever in the lower spine 500, and simultaneously no natural kyphosis, then there would be no need to utilize any treatment angle other than zero degrees.

The lower spine in 501 is acted upon by the resultant 502. The vertebral segments L5 511, and by way of the initial resultant 402 S1 510, are acted upon via the resultant 502 via the lower body harness 118 via the patient interface device 120.

The magnitude of the resultant tension 502 is set as a general guideline to ½ patient body weight as is customary in the art; however the healthcare provider is responsible for tuning this magnitude sufficient to lift the lower and rotate the lower patient body, sacrum/pelvis/hips, into position. The vertebral segments L5 511, and by way of 402 S1 510, are caused to lift and rotate relative to the inferior endplate of L4 512 per the vertical component Fy 504 of resultant tension 502. The angle of application 591 of resultant tension 502 is $\theta_2$-$\theta_1$, 540-530, plus that of 590, is sufficient to bring the posterior sides of the vertebral bodies L5 511 and L4 512 parallel to each other, and so into 'alignment'. Once the vertebral bodies L5 511 and L4 512, and by way of 402 S1 510 and L5 511, are aligned, the intervertebral discs are decompressed uniformly 581 and 580, anterior and posterior. Through the cycling of resultant tension 502, between maximal and minimal levels, the vertebral bodies L5 511 and L4 512, and S1 510 and L5 511, are brought into and out of alignment.

The benefits of decompressing, 580 and 581, and bringing into and out of alignment the vertebral bodies have been described in FIGS. 4A and 4B. It should be noted that according to this embodiment formed of the present invention, to align two vertebral bodies for the purpose of decompressing, increasing imbibition, and creating an interdiscal local nucleous pulposus pressure drop, it is required to first bring into alignment all distal vertebral segments, starting with S1 510 and L5 511.

Figure 6A:
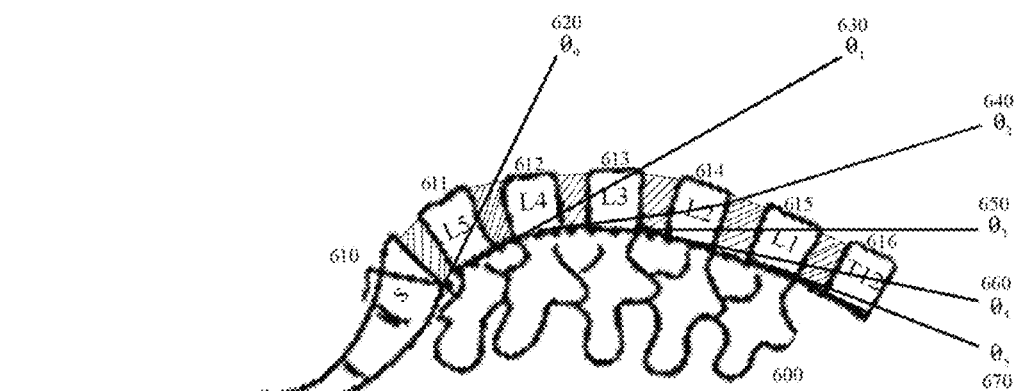
FIGS. 6A-6C illustrates three views of the coccyx, sacrum, and lumbar spine. The upper view represents the lower spine relaxed, before the application of tension at a specific angle. The second (middle) view represents the lower spine after the application of tension at an angle designed($\theta_T$) (using average or ideal spine radiographical models) to align the first sacral and fifth lumbar vertebra. The second view illustrates the first sacral vertebra rotated overly much upwards beyond alignment with the fifth lumbar vertebra by an angle ($\theta_{diff}$). The second view shows how the fifth lumbar vertebra L5 is rotating towards an unintended alignment with the fourth lumbar vertebra L4. The third (lowest) view shows the first sacral vertebra rotated downward by a subtractional angle ($\theta_{diff}$), adjusted during tension by the healthcare provider, sufficient to bring the first sacral vertebra into proper alignment with the fifth lumbar vertebra for that patient segmental angle ($\theta_1$-$\theta_0$), formed according to an embodiment of the present invention.
Figure 6B:
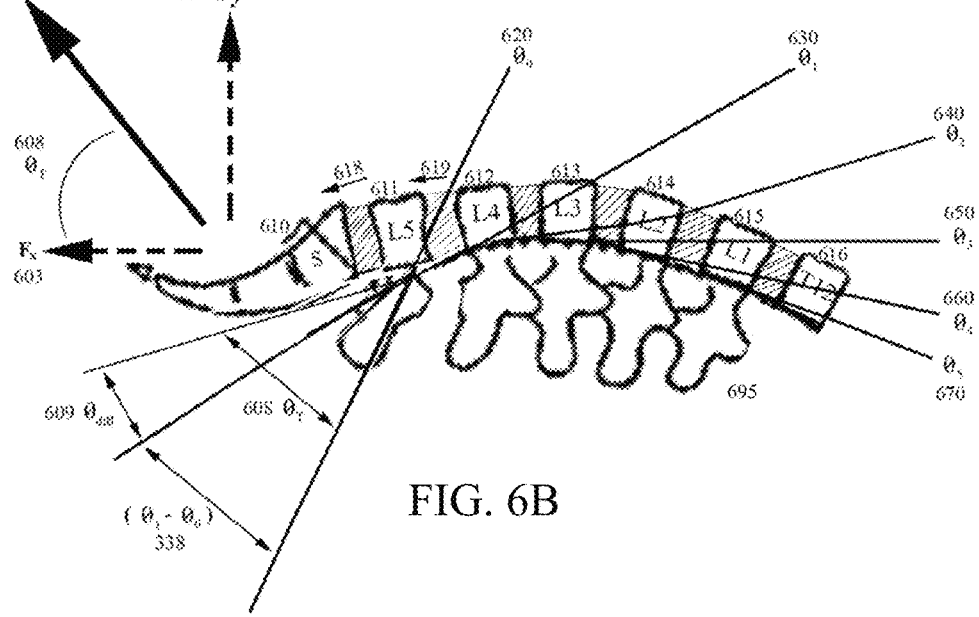
Figure 6C:
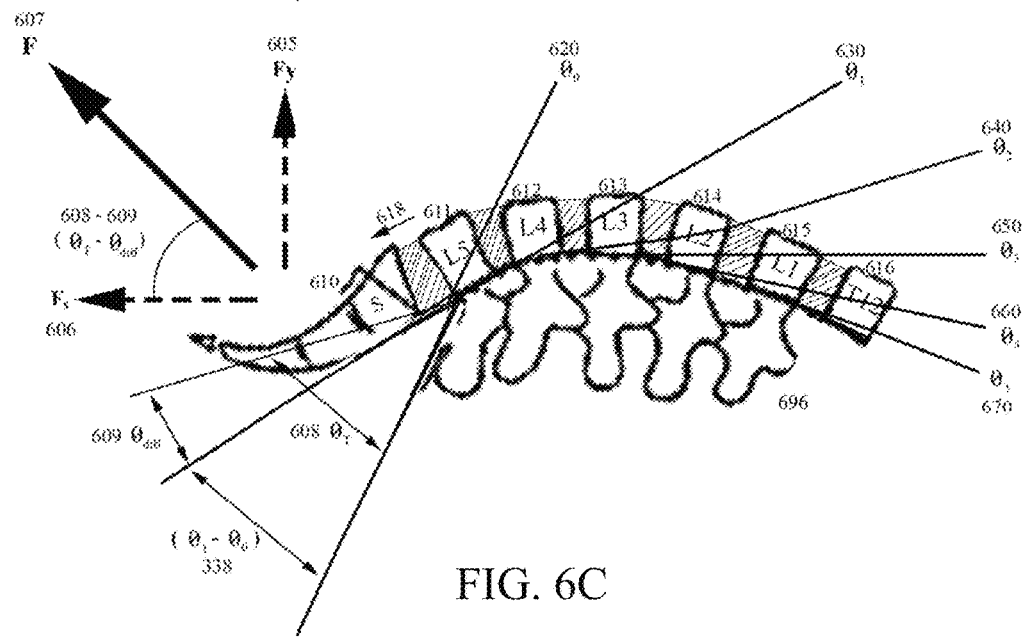

FIGS. 6A-6C illustrates three views of the coccyx (600, 695, 696). The upper view 600 represents the lower spine relaxed, before the application of resultant tension vector 602 at treatment angle ($\theta$T) 608. The second (middle) view 695 represents the lower spine after the application of resultant tension vector 602 at treatment angle ($\theta$T) 608 designed (using average or ideal spine radiographical models) to align the first sacral vertebra S1 610 and fifth lumbar vertebra L5 611. The third (lower) view 696 represents the lower spine after the application of resultant tension vector 607 at the treatment angle dynamically adjusted during tension to a reduced ($\theta$T) 608 −($\theta$diff) 609.

The HPT tangent lines 620, 630, 640, 650, 660, and 670 are drawn posterior to the vertebral bodies S1 610, L5 611, L4 612, L3 613, L2 614, and L1 615.

The resultant F 602 is applied to the patient 110 via the patient interface device 120 via the lower body harness 118 in the second view 695. The lower patient harness 118 is designed to originate the resultant tension vector F 602 at the base of the sacrum 610, underneath the supine patient 110 in this embodiment of the present invention. The resultant F 602, when broken down into a vertical Fy and horizontal Fx component 604 and 603, acts in two ways on the lower spine 600/695/696. First, the vertical component Fy 604 can be thought of as lifting, from the sacrum 610, countered by the third vertebra L3 613, the apex of lordosis, upon the center-top 310 of the lordotic support 112. The horizontal component Fx 603 can be thought of as pulling through the aligned spinal segments to elongate the spine.

In 600, none of the spinal segments 610, 611, 612, 613, 614, 615, and 616 have a segmental angle of zero (aligned) as there are no external forces acting on the spine and it is assumed some amount of lordosis is naturally present in between all segments of the lower spine in the patient. Were there no natural lordosis whatsoever in the lower spine 600, and simultaneously no natural kyphosis, then there would be no need to utilize any treatment angle other than zero degrees.

The lower spine in 695 is acted upon by the resultant 602. The vertebral segment S1 610 is acted upon via the resultant 602 via the lower body harness 118 via the patient interface device 120. The magnitude of the resultant tension 602 is set as a general guideline to ½ patient body weight as is customary in the art; however the healthcare provider is responsible for tuning this magnitude sufficient to lift the lower and rotate the lower patient body, sacrum/pelvis/hips, into position. The vertebral segment S1 610 is caused to lift and rotate relative to the inferior endplate of L5 611 per the vertical component Fy 604 of resultant tension 602.

The second view 695 illustrates the first sacral vertebra S1 610 rotated overly much upwards beyond alignment with the fifth lumbar vertebra L5 611 by treatment angle ($\theta_T$) 608. While treatment angle ($\theta_T$) 608 was designed for system 10 to bring only the first sacral vertebra S1 610 into alignment with the fifth lumbar vertebra L5 611, in this particular patient the treatment angle ($\theta_T$) 608 exceeds the patient's natural segmental angle L5-S1, ($\theta_1$-$\theta_0$) 338, by a difference of angle ($\theta_{diff}$) 609. The second view 695 shows how the fifth lumbar vertebra L5 611 is rotating towards an unintended alignment with the fourth lumbar vertebra L4 612. At the treatment angle ($\theta_T$) 608, resultant tension vector 602 is causing intentionally the first sacral vertebra S1 610 and the fifth lumbar vertebra L5 611 to align and elongate 618, and unintentionally the fifth lumbar vertebra L5 611 and fourth lumbar vertebra L4 612 to align and elongate 619.

The initial treatment angle ($\theta_T$) 608 of the resultant tension vector 602 produces the changes described above, at which point the healthcare provider may observe visually and by touch, and additionally by diagnostic equipment and/or patient feedback that L5 611 and L4 612 are unintentionally partially or wholly aligned and elongated 619. The healthcare provider may decide to dynamically adjust treatment angle ($\theta_T$) 608 under tension. As the treatment angle is adjusted dynamically, the healthcare provider can more accurately judge the proper segmental angle L5-S1, ($\theta_1$-$\theta_0$) 338, for that patient.

The third (lowest) view 696 shows the first sacral vertebra S1 610 rotated downward by angle ($\theta_{diff}$) 609, adjusted dynamically during tension by the healthcare provider, sufficient to bring the first sacral vertebra S1 610 into proper alignment with the fifth lumbar vertebra L5 611 for that patient's segmental angle ($\theta_1$-$\theta_0$) 338, formed according to an embodiment of the present invention. The new resultant tension vector 607 has the same magnitude as the initial resultant tension vector 602, but is applied to the patient 110 at a new treatment angle ($\theta_T$) 608 minus ($\theta_{diff}$) 609, equivalent to ($\theta_1$-$\theta_0$) 338.

By reducing the treatment angle ($\theta_T$) 608 by ($\theta_{diff}$) 609, the fifth lumbar vertebra L5 611 is no longer in alignment with the fourth lumbar vertebra L4 612. As L5 611 and L4 612 are not aligned, elongation 619 between L5 611 and L4 612 is minimized. The new treatment angle ($\theta_T$) 608 minus ($\theta_{diff}$) 609 maximizes elongation only at L5-S1, 618.

Figure 7A:
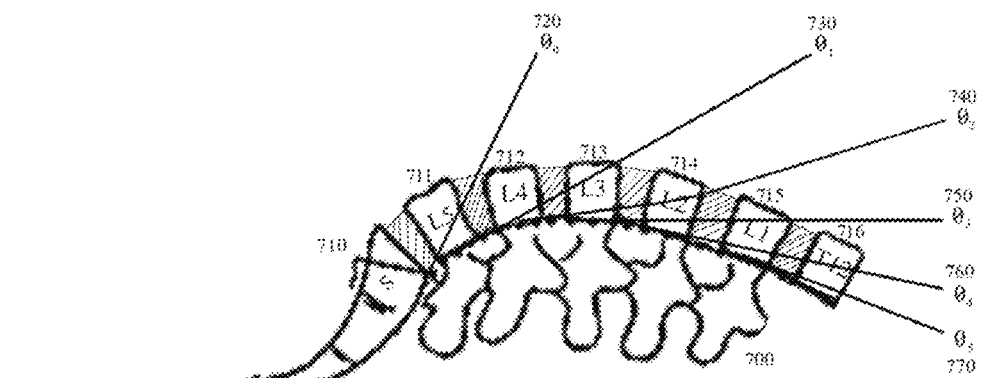
FIGS. 7A-7C illustrate three views of the coccyx, sacrum, and lumbar spine. The upper view represents the lower spine relaxed, before the application of tension at a specific angle. The second (middle) view represents the lower spine after the application of tension at an angle designed (using average or ideal spine radiographical models) to align the first sacral and fifth lumbar vertebra. The second view illustrates the first sacral vertebra rotated insufficiently upwards towards alignment with the fifth lumbar vertebra by an angle ($\theta_T$) designed to align the vertebra. The third (lowest) view shows the first sacral vertebra rotated upward by an additional angle ($\theta_{diff}$), adjusted during tension by the healthcare provider, sufficient to bring the first sacral vertebra in proper alignment with the fifth lumbar vertebra, formed according to an embodiment of the present invention.
Figure 7B:
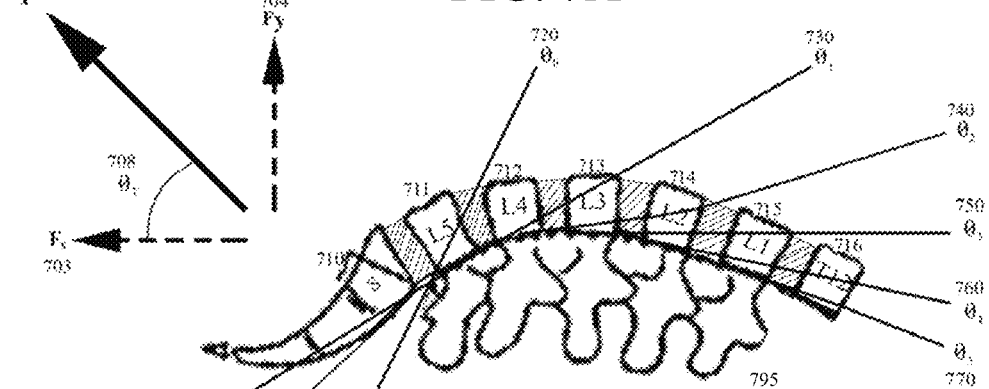
Figure 7C:
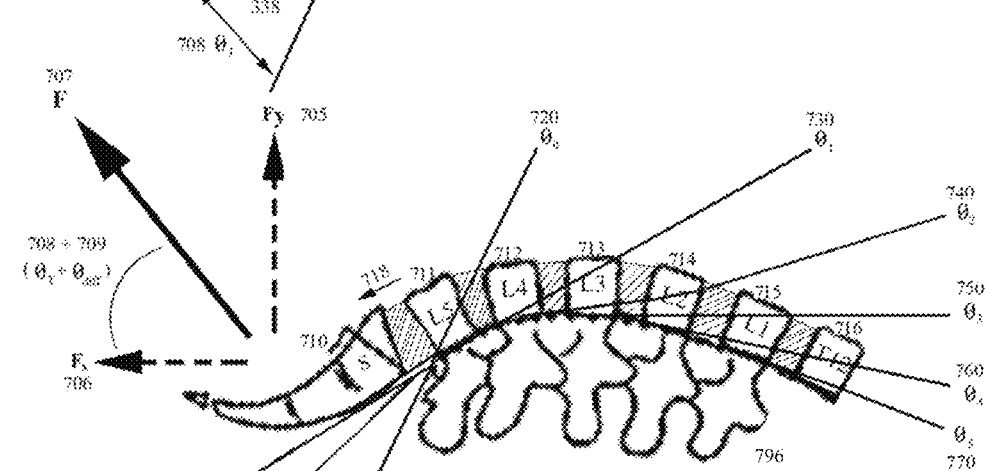

FIGS. 7A-7C illustrates three views of the coccyx(600, 695, 696). The upper view 700 represents the lower spine relaxed, before the application of resultant tension vector 702 at treatment angle ($\theta$T) 708. The second (middle) view 795 represents the lower spine after the application of resultant tension vector 702 at treatment angle ($\theta$T) 708 designed (using average or ideal spine radiographical models) to align the first sacral vertebra S1 710 and fifth lumbar vertebra L5 711. The third (lower) view 796 represents the lower spine after the application of resultant tension vector 707 at the treatment angle dynamically adjusted during tension to an increased ($\theta$T) 708+($\theta$diff) 709.

The HPT tangent lines 720, 730, 740, 750, 760, and 770 are drawn posterior to the vertebral bodies S1 710, L5 711, L4 712, L3 713, L2 714, and L1 715.

The resultant F 702 is applied to the patient 110 via the patient interface device 120 via the lower body harness 118 in the second view 795. The lower patient harness 118 is designed to originate the resultant tension vector F 702 at the base of the sacrum 710, underneath the supine patient 110 in this embodiment of the present invention. The resultant F 702, when broken down into a vertical Fy and horizontal Fx component 704 and 703, acts in two ways on the lower spine 700/795/796. First, the vertical component Fy 704 can be thought of as lifting, from the sacrum 710, countered by the third vertebra L3 713, the apex of lordosis, upon the center-top 310 of the lordotic support 112. The horizontal component Fx 703 can be thought of as pulling through the aligned spinal segments to elongate the spine.

In 700, none of the spinal segments 710, 711, 712, 713, 714, 715, and 716 have a segmental angle of zero (aligned) as there are no external forces acting on the spine and it is assumed some amount of lordosis is naturally present in between all segments of the lower spine in the patient. Were there no natural lordosis whatsoever in the lower spine 700, and simultaneously no natural kyphosis, then there would be no need to utilize any treatment angle other than zero degrees.

The lower spine in 795 is acted upon by the resultant 702. The vertebral segment S1 710 is acted upon via the resultant 702 via the lower body harness 118 via the patient interface device 120. The magnitude of the resultant tension 702 is set as a general guideline to ½ patient body weight as is customary in the art, however the healthcare provider is responsible for tuning this magnitude sufficient to lift the lower and rotate the lower patient body, sacrum/pelvis/hips, into position. The vertebral segment S1 710 is caused to lift and rotate relative to the inferior endplate of L5 711 per the vertical component Fy 704 of resultant tension 702.

The second view 795 illustrates the first sacral vertebra S1 710 rotated insufficiently upwards toward alignment with the fifth lumbar vertebra L5 711 by treatment angle ($\theta_T$) 708. While treatment angle ($\theta_T$) 708 was designed for system 10 to bring the first sacral vertebra S1 710 into alignment with the fifth lumbar vertebra L5 711, in this particular patient the treatment angle ($\theta_T$) 708 is less than the patient's natural segmental angle L5-S1, ($\theta_1-\theta_0$) 338, by a difference of angle ($\theta_{diff}$) 709. At the treatment angle ($\theta_T$) 708, resultant tension vector 702 is insufficient to cause the first sacral vertebra S1 710 and the fifth lumbar vertebra L5 711 to align and elongate.

The initial treatment angle ($\theta_T$) 708 of the resultant tension vector 702 produces the changes described above, at which point the healthcare provider may observe visually and by touch, and additionally by diagnostic equipment and/or patient feedback that S1 710 and L5 711 are not fully aligned and elongated. The healthcare provider may decide to dynamically adjust treatment angle ($\theta_T$) 708 under tension. As the treatment angle is adjusted dynamically, the healthcare provider can more accurately judge the proper segmental angle L5-S1, ($\theta_1-\theta_0$) 338, for that patient.

The third (lowest) view 796 shows the first sacral vertebra S1 710 rotated upward by angle ($\theta_{diff}$) 709, adjusted dynamically during tension by the healthcare provider, sufficient to bring the first sacral vertebra S1 710 into proper alignment with the fifth lumbar vertebra L5 711 for that patient's segmental angle ($\theta_1-\theta_0$) 338, formed according to an embodiment of the present invention. The new resultant tension vector 707 has the same magnitude as the initial resultant tension vector 702, but is applied to the patient 110 at a new treatment angle ($\theta_T$) 708 plus ($\theta_{diff}$) 709, equivalent to ($\theta_1-\theta_0$) 338.

By increasing the treatment angle ($\theta_T$) 708 by ($\theta_{diff}$) 709, the first sacral vertebra S1 710 and the fifth lumbar vertebra L5 711 are brought into alignment, maximizing elongation 719 between at L5-S1, 718.

Figure 8:
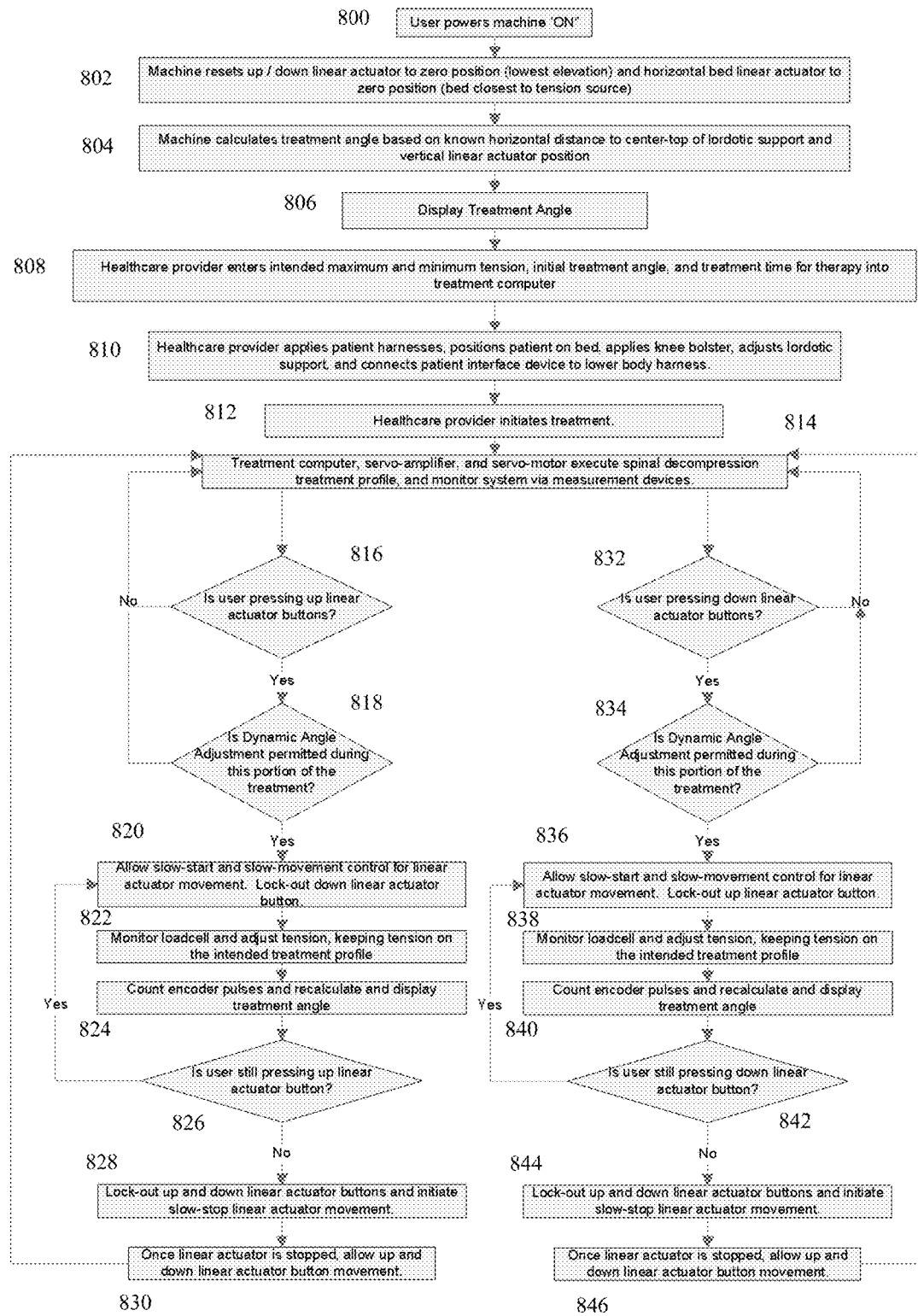
FIG. 8 illustrates a flowchart demonstrating an algorithm for adjusting treatment angle by a predetermined amount while not changing intended tension, formed according to an embodiment of the present invention.

FIG. 8 illustrates a flowchart demonstrating an algorithm for adjusting treatment angle by a predetermined amount while not changing intended tension, formed according to an embodiment of the present invention.

The algorithm proceeds from initial powering-on of the spinal decompression device 800. As part of the system 10 initialization routine 802, the vertical linear actuator 148 is reset to the lowest position. Any passive or active encoder data, or potentiometer data, relayed by an internally or externally mounted distance metering device relative to vertical linear actuator 148, will be measured against this initial zero point. Also as part of the system 10 initialization routine, the horizontal actuator 114 is reset to the position nearest the tension producing actuator 170. Any passive or active encoder data, or potentiometer data, relayed by an internally or externally mounted distance metering device relative to horizontal linear actuator 114, will be measured against this initial zero point 802. At this point the device calculates the initial treatment angle 804. Optionally, the device may employ absolute distance metering devices, which do not require the device to initialize vertical and horizontal actuators as in 802. Optionally, the device may commit to non-volatile memory the last known location of the vertical and horizontal linear actuators, and so not require initialization 802. The system of 10 then displays the treatment angle 806.

The healthcare provider may enter 808 into the treatment computer 190 the intended maximum and minimum tension for spinal decompression therapy. They may also enter the initial treatment angle and treatment time, among other parameters. This may be done before physical patient setup 810 as shown, or afterwards.

The healthcare provider then physically configures 810 the patient 110 upon the bed 100. The upper body harness 119 is secured to the head end of the bed 104. A knee bolster 117 is placed under the patient's knees. The bed 100 is adjusted horizontally and/or the patient 110 is adjusted on the bed 100 to locate the apex of lordosis, L3 250, over the center-top 310 of the lordotic support 112. The lower body harness 118 is connected to the patient interface device 120. The healthcare provider may then initiate treatment 812.

As treatment is initiated 812, the treatment computer 190 relays C treatment profile data, tension profile, to the servo-amplifier 192, which in-turn communicates B with the servo-motor 170, in this embodiment of the present invention. The tension producing actuator 170 rotates D, increasing tension on the patient interface device 120. The loadcell 150 registers tension, and relays E that metric to electronics 155. The electronics 155 relay A that information to the treatment computer 190. The treatment computer 190 sends updated tension profile information C to the servo-amplifier 192, completing a closed-loop feedback profile 814.

The healthcare provider may decide they want to increase or decrease treatment angle dynamically, under tension, after initiation of treatment 812. The healthcare provider would either want to increase treatment angle by pressing a button corresponding to vertical linear actuator 148 movement upwards 816, or want to decrease treatment angle by pressing a button corresponding to vertical linear actuator 148 movement downwards 832.

In the case of 816, treatment angle increase is indicated, and the treatment computer 190 decides if, based on software presets, dynamic angle adjustment is allowed 818. If dynamic angle adjustment is allowed 818, then the treatment computer 190 communicates A with electronics 155 to very slowly start and very slowly maintain vertical linear actuator 148 movement while the upwards-indicating vertical linear actuator button is pressed 820. In this embodiment of the present invention, no immediate or step transition in vertical linear actuator 148 movement is allowed. Once the upwards-indicating button is pressed 816, and for as long as it is pressed 826, the vertical linear actuator will continue to move slowly upwards 820. If the upwards-indicating button is no longer pressed, then the treatment computer 190 and electronics 155 will initiate a very slow stop of vertical linear actuator 148 movement 828. During that time 828, both the upward or downward indicating vertical linear actuator buttons are disabled 828. Once the vertical linear actuator 148 movement is stopped, as verified by distance metering devices, both the upward and downward indicating vertical linear actuator buttons are enabled 830.

While vertical linear actuator 148 movement is increasing treatment angle 820, the treatment computer 190 and electronics 155 continuously monitor the loadcell 155 information, and any other system 10 metrics, such that the magnitude of the resultant tension vector applied to the patient remains on its intended tension profile, while treatment angle is adjusted 822. As treatment angle is adjusted 820, the treatment computer 190 and electronics 155 monitor distance metering devices relative to the vertical linear actuator 148 and recalculate and display treatment angle 824.

It should be noted that treatment angle may be allowed to increase or decrease only by a small amount, based on perhaps one or more standard deviations away from average or ideal segmental angles for a particular treatment angle. Regardless of the bounds of dynamic angle adjustment amongst the full range of vertical linear actuator movement, as the vertical linear actuator approaches these bounds, it automatically slow-stops to avoid immediate change in treatment angle.

Once the actions 818, 820, 822, 824, 826, 828, and 830, as initiated by the healthcare provider 816, are completed, the device returns to monitoring the tension profile under assumed static vertical linear actuator 148 position 814.

In the case of 832, treatment angle decrease is indicated, and the treatment computer 190 decides if, based on software presets, dynamic angle adjustment is allowed 834. If dynamic angle adjustment is allowed 834, then the treatment computer 190 communicates A with electronics 155 to very slowly start and very slowly maintain vertical linear actuator 148 movement while the downwards-indicating vertical linear actuator button is pressed 836. In this embodiment of the present invention, no immediate or step transition in vertical linear actuator 148 movement is allowed. Once the downwards-indicating button is pressed 832, and for as long as it is pressed 842, the vertical linear actuator will continue to move slowly downwards 836. If the downwards-indicating button is no longer pressed, then the treatment computer 190 and electronics 155 will initiate a very slow stop of vertical linear actuator 148 movement 844. During that time 844, both the upward or downward indicating vertical linear actuator buttons are disabled 844. Once the vertical linear actuator 148 movement is stopped, as verified by distance metering devices, both the upward and downward indicating vertical linear actuator buttons are enabled 846.

While vertical linear actuator 148 movement is decreasing treatment angle 836, the treatment computer 190 and electronics 155 continuously monitor the loadcell 155 information, and any other system 10 metrics, such that the magnitude of the resultant tension vector applied to the patient remains on its intended tension profile, while treatment angle is adjusted 838. As treatment angle is adjusted 836, the treatment computer 190 and electronics 155 monitor distance metering devices relative to the vertical linear actuator 148 and recalculate and display treatment angle 840.

Once the actions 834, 836, 838, 840, 842, 842, 846, and 830, as initiated by the healthcare provider 832, are completed, the device returns to monitoring the tension profile under assumed static vertical linear actuator 148 position 814.

Figure 9:
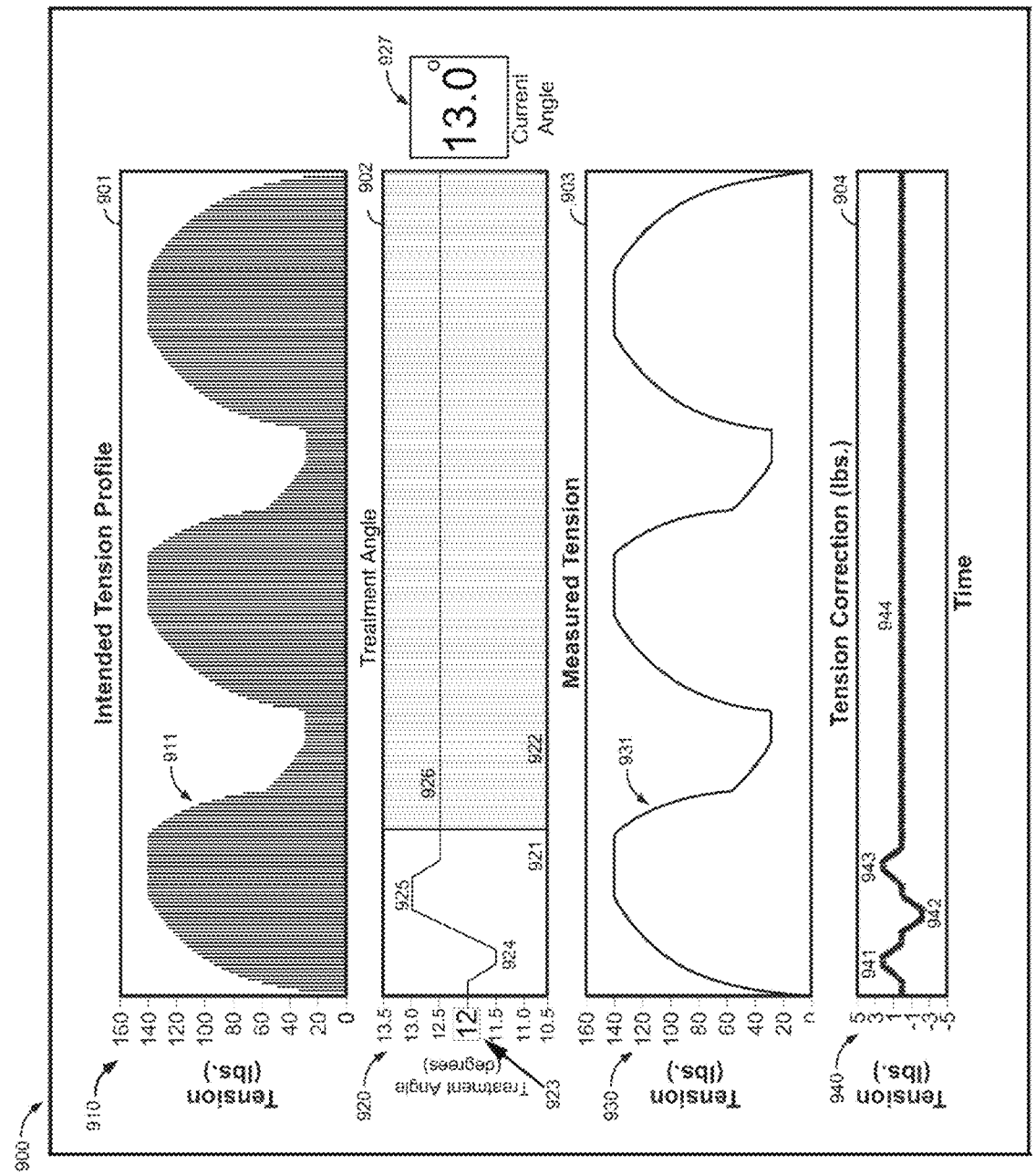
FIG. 9 illustrates a spinal decompression treatment graph, showing intended tension, treatment angle, measured tension, and tension correction versus time, formed according to an embodiment of the present invention.

FIG. 9 represents a treatment screen 900 as may be displayed on the spinal decompression device of system 10 and/or printed. In 900, four graphs 901, 902, 903, and 904 are shown, vertically aligned, all plotted against the same horizontal scale (time).

In 901, the intended tension profile is shown. In this embodiment of the present invention, the intended tension profile is a series of maximum and minimum tension level plateaus, connected by logarithmic increases and decreases in tension 911. The y-axis 910 for 901 is tension, plotted in pounds, shown from zero to 160 lbs. From the plot 901, the maximum tension plateaus are 140 lbs., and the minimum tension plateaus are 30 lbs.

In 902, the treatment angle is plotted versus time. The y-axis 920 is treatment angle, plotted in degrees. The y-axis 920 is centered about the initial treatment angle 923, 12°, which is shown enlarged and bounded for clarity. In this embodiment of the present invention, 12° is the setting for the L5-S1 intervertebral space, and the first standard deviation of segmental angles for L5-S1 are plus and minus 1.5°. In this embodiment of the present invention, the bounds for dynamic angle adjustment are one standard deviation away from the spinal decompression device's designed treatment angles.

In 902, as treatment is initiated, the healthcare provider is able to dynamically adjust tension for a period including up to the end of the first maximum tension plateau 921. Beyond 921, the ability to dynamically adjust treatment angle is disabled 922, as set in software, in this embodiment of the present invention. As treatment is initiated, the healthcare provider dynamically adjust treatment angle downward 0.5° 924. The healthcare provider then adjusts treatment angle 2° upwards to 13.0° 925. The healthcare provider then adjusts treatment angle downwards to 12.5° 926, where it is maintained for the rest of the treatment.

The current treatment angle 927 is displayed in a box to the right of 902. This display 927 changes and is updated as treatment angle is changed.

In 903, the measured tension 931 is displayed, as relayed by the loadcell 155 in this embodiment of the present invention but that may be relayed by any load or torque sensing device. The measured tension 931 is plotted against y-axis 930 in lbs. which is the same as scale 910. It should be noted that, according to this embodiment of the present invention, measured tension 931 is the same as intended tension profile 911, even during dynamic angle adjustment period 921.

In 904, tension correction 944 is displayed. Tension correction 944 is plotted against y-axis 940 in lbs. In the system 10 formed of one embodiment of the present invention, as treatment angle is adjusted downwards 924, tension must be increased momentarily 941 to counteract changes in system dynamics and system mechanical advantages, keeping measured tension 931 the same as intended tension 911. In the system 10 formed of one embodiment of the present invention, as treatment angle is adjusted upwards 925, tension must be decreased momentarily 942 to counteract changes in system dynamics and system mechanical advantages, keeping measured tension 931 the same as intended tension 911. In the system 10 formed of one embodiment of the present invention, as treatment angle is adjusted downwards 926, tension must be increased momentarily 943 to counteract changes in system dynamics and system mechanical advantages, keeping measured tension 931 the same as intended tension 911. Variations in the design of spinal decompression devices may change the way the system's 10 tension producing actuator 170 reacts to changes in treatment angle, as reflected in that particular system's 10 tension correction profile for a treatment period 904.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof It is intended that the scope of the invention be defined by the Claims appended hereto and their equivalents.

What is claimed is:

1. A tensioning device, comprising:
    a patient positioning means configured to precisely, repeatedly align a target region of a patient spine;
    a tension producing actuator configured to place the patient spine in tension;
    a positioning device operationally configured to position the tension producing actuator relative to the target region of the patient spine;
    a patient interface device operationally configured to interface the tension producing actuator with the patient spine;
    a control system with feedback on a resultant tension vector applied to the patient spine operationally configured to allow for adjustment of either tension producing actuator position, patient position, or both while applying tension to the patient spine during non-therapeutic tension levels; and
    a display operationally configured to provide geometric data regarding the resultant tension vector to a user or healthcare provider;
    wherein the control system automatically adjusts tension producing actuator work levels such that a resultant tension vector magnitude remains ideally constant during adjustment of a resultant tension vector angle, reducing risk of eliciting paraspinal muscle contraction due to changes in the resultant tension vector magnitude.

2. The device of claim 1, wherein the patient positioning means includes a patient bed, wherein a region of the patient bed is identified as an alignment region over which the target region of the patient spine should be positioned.

3. The device of claim 2, wherein the patient bed includes physically removable portions of a bed body and a series of physical devices related to a treatment attached thereof.

4. The device of claim 1, wherein the tension producing actuator includes an electro-mechanical device which generates torque through rotation.

5. The device of claim 4, wherein the tension producing actuator includes a means of increasing or decreasing torque generated.

6. The device of claim 5, wherein the positioning device includes a removable positioning means by which increases and decreases in the height of the tension producing actuator relative to the target region of the patient spine are accomplished.

7. The device of claim 1, wherein the patient interface device includes a strap connected to a patient harness, one end of the strap includes a connection to a rotation of the tension producing actuator, and a connection to the patient harness at its opposite end, the patient harness adapted to cradle a portion of a patient pelvis and the patient spine.

8. The device of claim 7, wherein the patient interface device is operationally configured to translate decompression tension generated by torque generated by the tension producing actuator to the patient spine.

9. The device of claim 6, wherein the control system allows for a user or healthcare provider input and includes a means to set, generate, and keep ideally constant the resultant tension vector magnitude during which either the resultant tension vector angle or a patient spine target region position, relative to a location on the tensioning device, is adjusted by the user or healthcare provider.

10. The device of claim 9, wherein the control system allows for the user or healthcare provider to modify the resultant tension vector angle while tension is applied to the patient spine, the resultant tension vector magnitude kept ideally constant, while the patient spine target region position, relative to the location on the tensioning device, is unchanged.

11. The device of claim 9, wherein the control system allows for the user or healthcare provider to modify the patient spine target region position, relative to the location on the tensioning device, while tension is applied to the patient spine, the resultant tension vector magnitude kept ideally constant, while the tension producing actuator position, relative to the location on the tensioning device, is unchanged.

12. The device of claim 9, wherein the control system allows for the user or healthcare provider to set the resultant tension vector angle and to modify the patient spine target region position, relative to the location on the tensioning device, while tension is applied to the patient spine, the resultant tension vector magnitude kept ideally constant, the control system automatically adjusting the tension producing actuator position, relative to the location on the tensioning device, to maintain a user-set resultant tension vector angle.

13. The device of claim 9, wherein the control system includes a display or means for communicating the resultant tension vector angle and magnitude to the user or healthcare provider.

14. The device of claim 13, wherein the control system allows for the user or healthcare provider to visually assess, physical palpitate, or verbally or otherwise receive feedback from a patient to modify the patient position and to achieve a concentration of the resultant tension vector magnitude near a vertebral area of interest during the applied ideally constant resultant tension vector magnitude.

15. The device of claim 14, wherein the control system indicates a location of the patient spine where resultant tension is concentrated based on empirical calculation of said location relative to a spinal model and mathematical and medical assumptions.

16. The device of claim 15, where the control system calculates the location of the spine where resultant tension is concentrated based on ideal spine models arrived at through clinically cited spinal morphology studies.

17. The device of claim 16, wherein the user or healthcare provider is able to visually assess, palpitate, and/or query the patient to determine optimum pre-treatment treatment angle or resultant tension vector angle while reducing risk associated with eliciting a paraspinal muscle contraction due to changes in resultant tension vector magnitude.

* * * * *